(12) United States Patent
Hayashi et al.

(10) Patent No.: US 10,401,276 B2
(45) Date of Patent: Sep. 3, 2019

(54) METHOD FOR GENERATING THREE-DIMENSIONAL LUMINESCENCE IMAGE, AND IMAGING SYSTEM

(71) Applicant: OLYMPUS CORPORATION, Tokyo (JP)

(72) Inventors: Taro Hayashi, Tachikawa (JP); Yoko Ohashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 75 days.

(21) Appl. No.: 15/647,486

(22) Filed: Jul. 12, 2017

(65) Prior Publication Data

US 2017/0315049 A1    Nov. 2, 2017

Related U.S. Application Data

(63) Continuation of application No. PCT/JP2015/051698, filed on Jan. 22, 2015.

(30) Foreign Application Priority Data

Jan. 22, 2015  (WO) .................. PCT/JP2015/051698

(51) Int. Cl.
*G01N 15/14* (2006.01)
*G01N 21/76* (2006.01)
(Continued)

(52) U.S. Cl.
CPC ..... *G01N 15/1475* (2013.01); *G01N 15/1434* (2013.01); *G01N 21/763* (2013.01);
(Continued)

(58) Field of Classification Search
CPC ............. G01N 15/1475; G01N 21/763; G01N 33/4833; G01N 15/1434; G01N 2015/0065; G01N 2015/1452; G01N 2015/1445; G01N 2015/1006; H04N 5/23212; H04N 5/265; G03B 13/34
See application file for complete search history.

(56) References Cited

U.S. PATENT DOCUMENTS

| 2009/0323059 A1 | 12/2009 | Sun et al. | |
|---|---|---|---|
| 2010/0189341 A1* | 7/2010 | Oota .................... | A61B 1/0019 382/154 |
| 2014/0232931 A1* | 8/2014 | Oda ....................... | H04N 5/232 348/371 |

FOREIGN PATENT DOCUMENTS

| CN | 101822526 A | 9/2010 |
|---|---|---|
| JP | 2003-057170 A | 2/2003 |

(Continued)

OTHER PUBLICATIONS

English translation of International Preliminary Report on Patentability dated Aug. 3, 2017 together with the Written Opinion received in related International Application No. PCT/JP2015/051698.

(Continued)

*Primary Examiner* — Yogesh K Aggarwal
(74) *Attorney, Agent, or Firm* — Scully, Scott, Murphy & Presser, P.C.

(57) ABSTRACT

A method for generating a three-dimensional luminescence image includes setting a focal interval between two-dimensional images in accordance with localization of luminescence in a three-dimensional sample. The three-dimensional sample contains a plurality of cells prepared to be luminescent and has a three-dimensional shape. The two-dimensional images have mutually different focal planes and are acquired at the focal interval. The method further includes acquiring a two-dimensional image set including two-dimensional images at the focal interval that is set by imaging the three-dimensional sample under an unirradiated condition; and generating a three-dimensional luminescence image by combining the two-dimensional images included in the two-dimensional image set together.

9 Claims, 19 Drawing Sheets

(51) Int. Cl.
- *G01N 33/483* (2006.01)
- *G03B 13/34* (2006.01)
- *H04N 5/232* (2006.01)
- *H04N 5/265* (2006.01)
- *G01N 15/00* (2006.01)
- *G01N 15/10* (2006.01)

(52) U.S. Cl.
CPC ......... *G01N 33/4833* (2013.01); *G03B 13/34* (2013.01); *H04N 5/23212* (2013.01); *H04N 5/265* (2013.01); *G01N 2015/0065* (2013.01); *G01N 2015/1006* (2013.01); *G01N 2015/1445* (2013.01); *G01N 2015/1452* (2013.01)

(56) References Cited

FOREIGN PATENT DOCUMENTS

| | | |
|---|---|---|
| JP | 2006-308808 A | 11/2006 |
| JP | 2006-320335 A | 11/2006 |
| JP | 2010-532487 A | 10/2010 |
| JP | 2012-022135 A | 2/2012 |
| JP | 2012-122829 A | 6/2012 |
| JP | 5424528 B2 | 2/2014 |
| JP | 2014-089193 A | 5/2014 |
| JP | 2014-119762 A | 6/2014 |

OTHER PUBLICATIONS

English translation of International Preliminary Report on Patentability dated Aug. 3, 2017 together with the Written Opinion received in related International Application No. PCT/JP2016/051679.

International Search Report dated Apr. 5, 2016 issued in PCT/JP2016/051679.

International Search Report dated Apr. 7, 2015 issued in PCT/JP2015/051698.

English Abstract of JP 2008-089521, dated Apr. 17, 2008.

Chinese Office Action dated Mar. 29, 2019 in Chinese Patent Application No. 201680006671.6.

\* cited by examiner

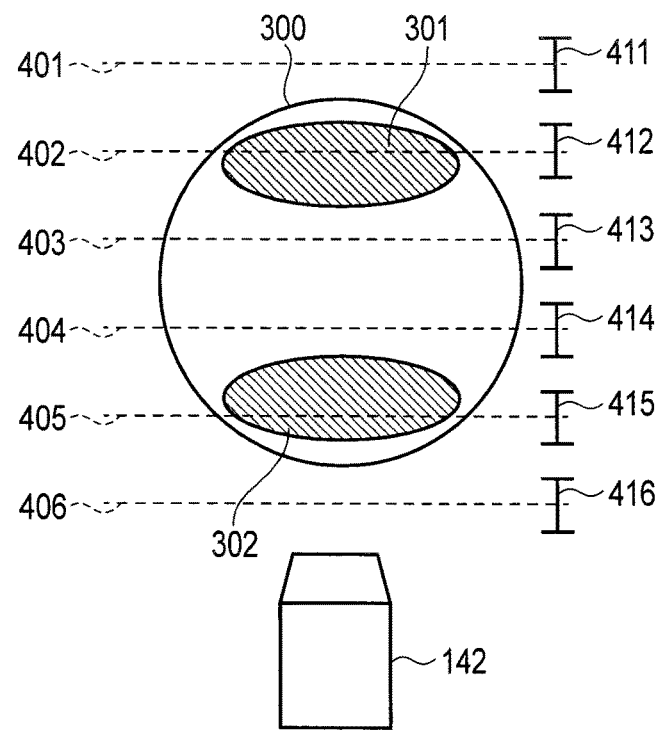
F I G. 9
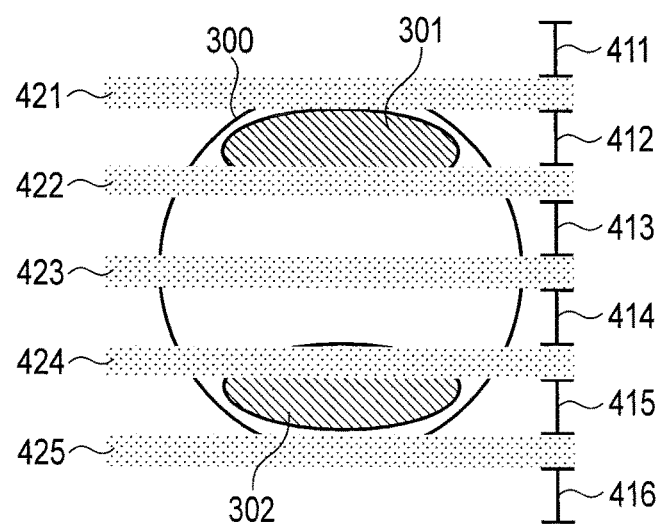
F I G. 10

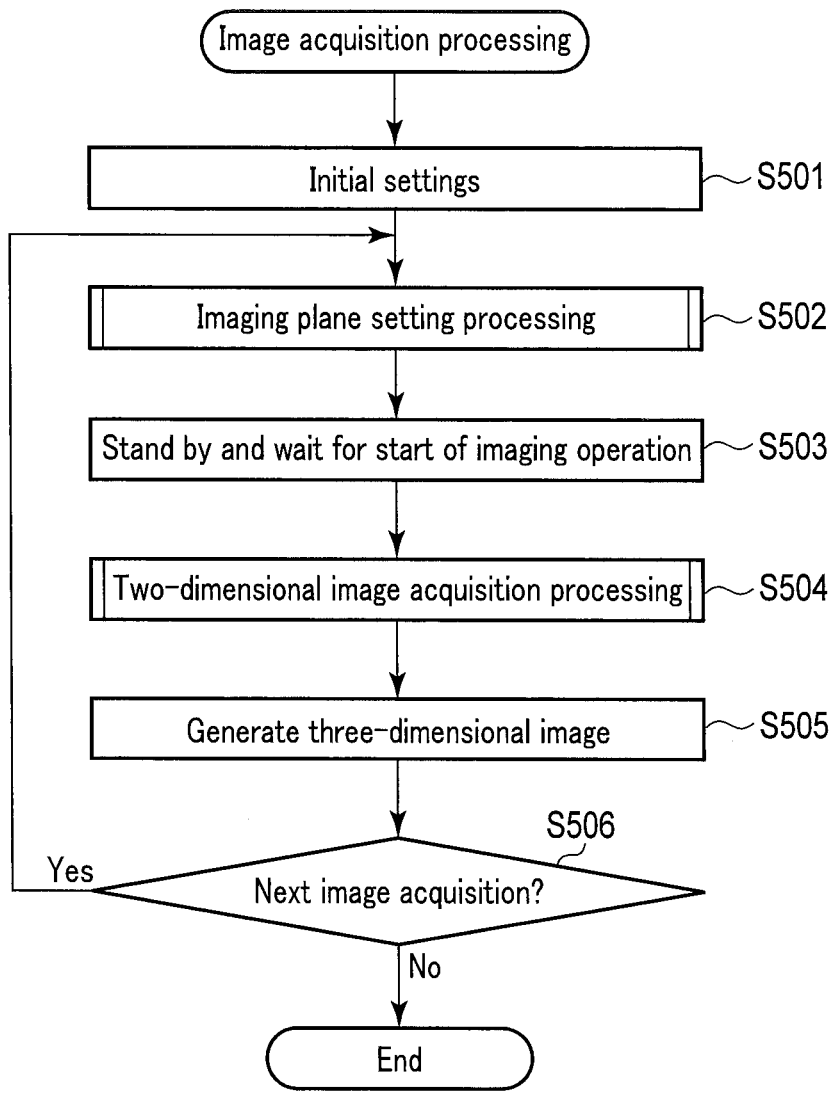
F I G. 15

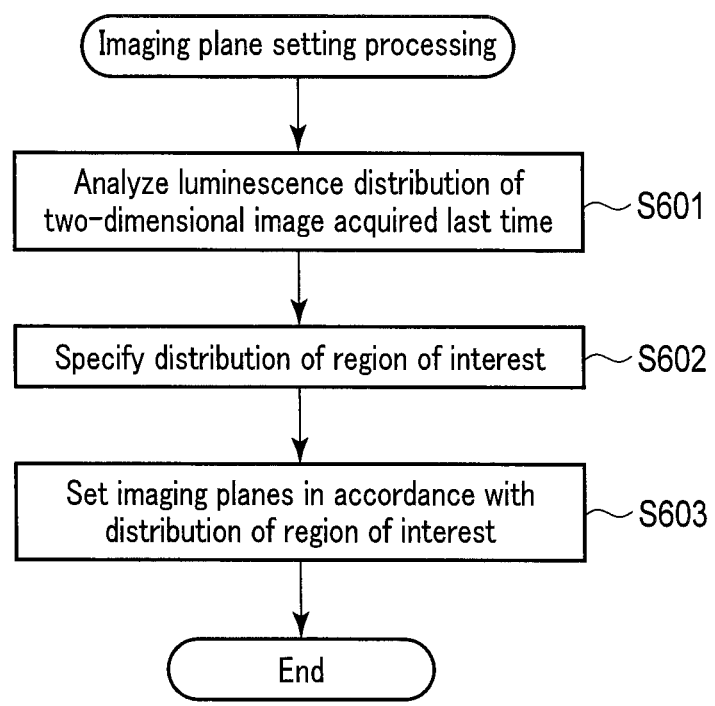
F I G. 16

METHOD FOR GENERATING THREE-DIMENSIONAL LUMINESCENCE IMAGE, AND IMAGING SYSTEM

CROSS-REFERENCE TO RELATED APPLICATIONS

This application is a Continuation Application of PCT Application No. PCT/JP2016/051679, filed Jan. 21, 2016 and based upon and claiming the benefit of priority from prior PCT Application No. PCT/JP2015/051698, filed Jan. 22, 2015, the entire contents of all of which are incorporated herein by reference.

BACKGROUND OF THE INVENTION

1. Field of the Invention

The present invention relates to a method for generating a three-dimensional luminescence image, and an imaging system for generating a three-dimensional luminescence image.

2. Description of the Related Art

In recent years, embryoid bodies or spheroids derived from stem cells, such as iPS cells or ES cells, are attracting attention as new research subjects, and researches are being made using them. In general, embryoid bodies or spheroids derived from stem cells are a cluster of cells which are an aggregation of stem cells cultured in a non-adhesive state and which form a spherical three-dimensional structure. Cells included in embryoid bodies or spheroids are capable of differentiating into various cells in accordance with culturing conditions. For example, in the field of regenerative medicine intended to regenerate organs or in the field of drug discovery in which the medicinal effect and toxicity of a new drug are evaluated, the use of cells that have a three-dimensional structure similar to the environment inside the body is preferable to the use of cells that are cultured in two dimensions. For this reason, embryoid bodies or spheroids derived from stem cells are attracting attention as research substances in the field of recent regenerative medicine or drug discovery.

In the conventional evaluation of two-dimensional cultured cells, cells are marked with a luminescent protein or a fluorescent protein, and the luminescence or fluorescence is detected to detect what is happening in the cells (e.g., Jpn. Pat. Appln. KOKAI Publications No. 2014-89193 and No. 2006-320335). In the research using embryoid bodies having a 3D structure, an observation method that enables accurate understanding of the state of the embryoid bodies, such as the degree of differentiation, is desired. Desirably, changes inside the embryoid bodies should be observed in three dimensions.

For example, Japanese Patent No. 5424528 discloses an analysis method and an analysis system. The method and system use, as thick living samples, embryos or tissues which generate a feeble light and contain a number of measurement portions. In the method and system, feeble light signals are acquired at different positions depending upon the measurement portions, and analysis is performing based on the signals. For example, Jpn. Pat. Appln. KOKAI Publication No. 2014-119762 discloses a microscope system which takes a bright field image and a luminescence image or fluorescence image while changing the focus position.

In the analysis of the interior of a three-dimensional sample, a plurality of two-dimensional images having different focal planes are acquired by performing an imaging operation while shifting the focal position at regular intervals, and reconstruction processing performed based on such two-dimensional images generates a three-dimensional image. It is known in the art that the generation of such a three-dimensional image enables analysis of the internal structure of a 3D sample and analysis of how the internal structure changes (for example, see Jpn. Pat. Appln. KOKAI Publication No. 2012-122829 and Jpn. PCT National Publication No. 2010-532487). In this case, cells labelled with a luminescent protein or a fluorescent protein are used, and various information on living cells can be acquired.

For example, where the analysis of gene expression inside embryoid bodies is performed by the conventional fluorescent observation method, the phototoxicity of excitation light or the influence of autofluorescence may cause undesirable phenomena. In addition, the excitation light may not reach the interior of an embryoid body if the embryoid body is large to a certain degree. In contrast, where the luminescent observation using a luminescent protein is used, the interior of a thick sample, such as an embryoid body, can be observed without being affected by the phototoxicity of excitation light or the influence of autofluorescence.

However, the luminescence intensity of a luminescent protein is generally lower than the fluorescence intensity of a fluorescent protein, and a long-time exposure is required for one-time imaging. For this reason, the method in which a three-dimensional luminescence image is generated by reconstructing luminescence images which are taken, with the focal position shifted at regular intervals, has problems in that image formation inevitably takes time. If imaging intervals related to the focal positions are short when a plurality of two-dimensional images are taken, a three-dimensional image includes a large amount of information and has a high resolution. At the same time, however, the total of imaging time is long, and the data size increases. Conversely, if the imaging intervals related to the focal positions are long, the data size decreases, but the amount of information included in a three-dimensional image decreases, and the resolution lowers.

For example, where the medicinal efficiency and toxicity of a new drug are evaluated using embryoid bodies, the time before a reaction takes place in the embryoid bodies may be long, depending upon which compound should be evaluated. In addition, the reaction may change over a long duration. Therefore, a long-time observation may be required. Where the process of differentiation in which embryoid bodies differentiate into various cells, including cardiac muscle cells and liver cells, a long-time observation may be required.

BRIEF SUMMARY OF THE INVENTION

According to an aspect of the invention, a method for generating a three-dimensional luminescence image includes setting a focal interval between two-dimensional images in accordance with localization of luminescence in the three-dimensional sample, the three-dimensional sample containing a plurality of cells prepared to be luminescent and having a three-dimensional shape, the two-dimensional images having mutually different focal planes; acquiring a two-dimensional image set including the two-dimensional images at the set focal interval by imaging the three-dimensional sample under an unirradiated condition; and generating a three-dimensional luminescence image by combining the two-dimensional images included in the two-dimensional image set together.

According to an aspect of the invention, an imaging system includes an objective optical system; a drive unit which moves a focus position of the objective optical system in an optical axis direction; an imaging unit which is configured to take, by use of the objective optical system, a luminescence image of a three-dimensional sample, the three-dimensional sample containing a plurality of cells prepared to be luminescent and having a three-dimensional shape; an interval setting unit which, when a plurality of two-dimensional images having mutually different focal planes are acquired, sets a focal interval between the two-dimensional images in accordance with localization of luminescence in the three-dimensional sample; an imaging control unit which causes the imaging unit to image the three-dimensional sample while controlling the drive unit under an unirradiated condition, thereby acquiring a two-dimensional image set including the two-dimensional images obtained at the focal interval; and an image synthesis unit which generates a three-dimensional luminescence image by combining the two-dimensional images included in the two-dimensional image set together.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 9 is a schematic diagram for explaining how image acquisition of a three-dimensional sample is performed according to the second embodiment and showing the case where the interval between imaging planes is longer greater than the depth of focus of an objective optical system.

FIG. 10 is a schematic diagram for explaining a three-dimensional image obtained according to the second embodiment.

FIG. 15 is a flowchart illustrating an example of image acquisition processing according to the second embodiment.

FIG. 16 is a flowchart illustrating an example of imaging plane setting processing according to the second embodiment.

DETAILED DESCRIPTION OF THE INVENTION

First Embodiment

Figure 1:
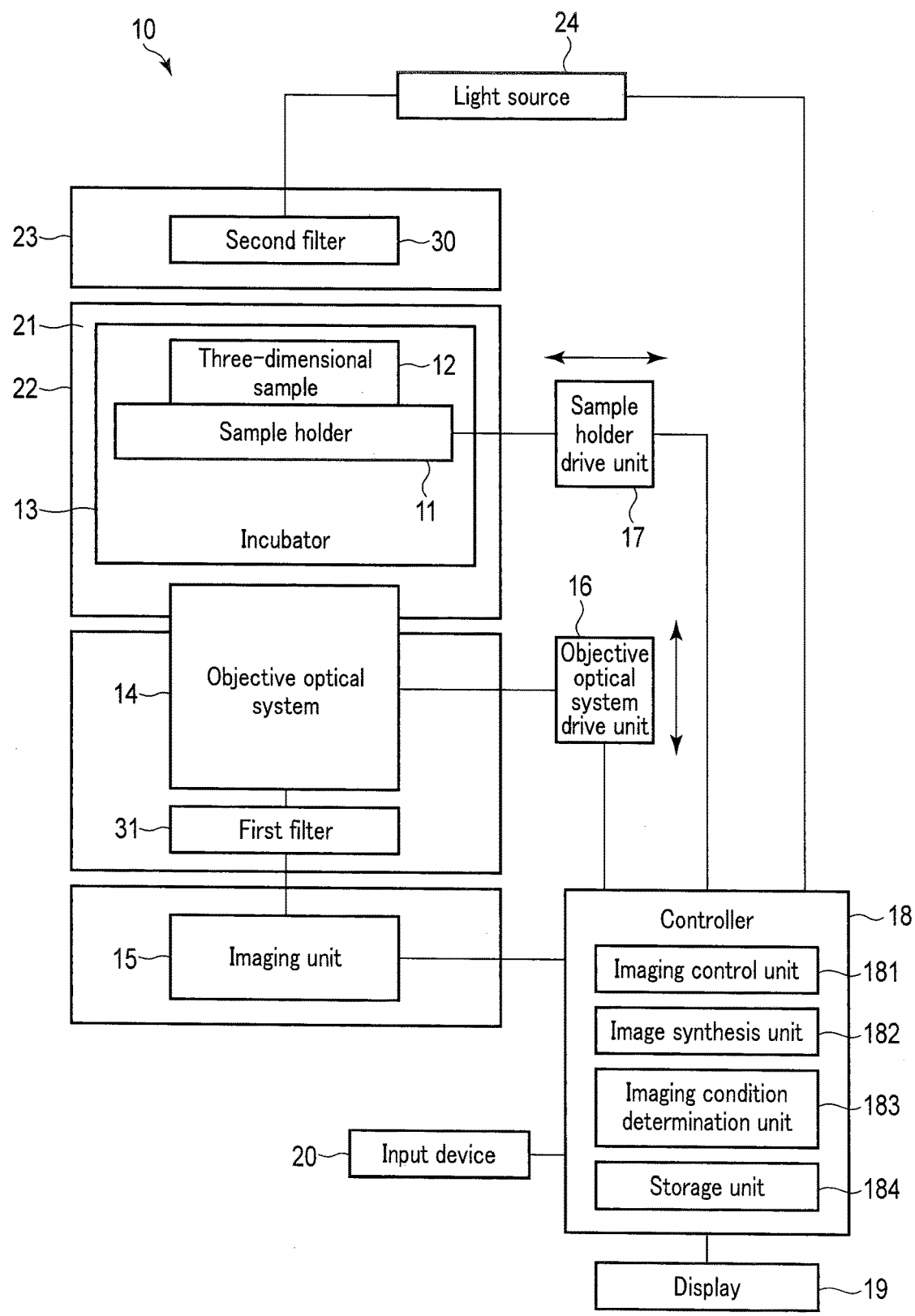
FIG. 1 is a block diagram schematically showing an exemplary configuration of an imaging system according to one embodiment of the present invention.

The first embodiment of the present invention will now be described with reference to the accompanying drawings. FIG. 1 schematically illustrates an exemplary configuration of an imaging system for acquiring a three-dimensional luminescence image according to the present embodiment. As shown in FIG. 1, the imaging system 10 includes a sample holder 11 for holding a three-dimensional sample 12, an incubator 13, an objective optical system 14, an imaging unit 15, an objective optical system drive unit 16, a sample holder drive unit 17, a controller 18 for controlling each portion of the imaging system 10, a display 19 and an input device 20.

The three-dimensional sample 12 is a thick sample containing a plurality of cells. The sample 12 is, for example, an embryoid body or a spheroid derived from a stem cell, such as an iPS cell or ES cell. The three-dimensional sample 12 is prepared to be self-luminescent under a condition where it is not irradiated with light. The three-dimensional sample 12 contains cells into which a luciferase gene is introduced.

When luciferin is added, cells in which luciferase is expressed become luminescent.

The incubator 13 adjusts conditions of the cell sustaining environment of the three-dimensional sample 12, such as the temperature and $CO_2$ concentration. The objective optical system 14 includes an optical system similar to a general type of microscope, such as an objective lens. The imaging unit 15 includes an imaging device, such as a cooled CCD camera. The imaging element included in the imaging unit 15 is not limited to a CCD image sensor; it may be a CMOS image sensor or the like. The imaging unit 15 takes an image of the three-dimensional sample 12 enlarged by the objective optical system 14. The imaging unit 15 takes an image of the three-dimensional sample 12 in an unirradiated state, so that it can acquire an image showing how the three-dimensional sample 12 is luminescent. An image showing the luminescence will be referred to as a luminescence image.

A first filter 31 may be provided between the objective optical system 14 and the imaging unit 15. The first filter 31 is, for example, a spectral film. Where one or two or more kinds of luminescent protein emitting light of difference wavelengths are used as the luminescent protein (e.g., luciferase) for the luminescence of the interior of cells, imaging may be performed for each of the wavelengths. In this case, the first filter 31 is used for separating light according to the wavelengths. Images may be taken, with the first filter 31 changed from one to another. Alternatively, different imaging units may be employed for the respective wavelengths, or imaging may be performed simultaneously at different partial regions on an imaging element. As a result, a multi-color three-dimensional luminescence image can be acquired.

The sample holder 11 is configured to hold the three-dimensional sample 12. The sample holder 11 is configured to be movable in the planar directions (X-Y directions). The sample holder 11 is, for example, a stage. The sample holder drive unit 17 moves the sample holder 11 in the planar directions (X-Y directions). Since the sample holder 11 moves in the planar directions (X-Y directions), the field of view for imaging can be changed in the plane.

The objective optical system drive unit 16 changes the focus position in the optical axis direction (Z direction), which is perpendicular to the planar directions (X-Y directions) of the objective optical system 14. The objective optical system drive unit 16 moves, for example, an objective lens in the optical axis direction. The sample holder 11 may be moved in the optical axis direction by the sample holder drive unit 17, instead of the objective optical system drive unit 16. Since the focus position is changed by the objective optical system drive unit 16, images in which positions different in the thickness direction of the three-dimensional sample 12 are focused can be acquired.

The imaging system 10 includes a main body 21 provided with both the sample holder 11 and the incubator 13, a dark box 22 provided around the outer periphery of the main body 21, a lid 23 covering the dark box 22, a second filter 30 provided for the lid 23, and a light source 24 (which emits illumination light falling on the three-dimensional sample 12 via the second filter 30). The interior of the main body 21 is shielded from external light by the dark box 22 and the lid 23. When the light source 24 is turned off, the interior of the main body 21 is under the condition where no illumination light is irradiated. With this structure, even when the three-dimensional sample 12 inside the main body 21 is emitting a very feeble light, the imaging system 10 can take an image of that light under a desirable condition. When the light source 24 is turned on, the three-dimensional sample 12 is irradiated with light. The three-dimensional sample 12 is observed under a light irradiated condition so as to confirm the position of the sample prior to the observation and imaging of luminescence and to adjust the focal position on the surface of the sample.

Excitation light for generating fluorescence can be radiated to the three-dimensional sample 12 by using the second filter 30 configured as a spectral film or by employing a laser light source as the light source 24. If the three-dimensional sample 12 is prepared to be fluorescent, not only an image of the luminescence but also an image of the fluorescence of the three-dimensional sample 12 can be acquired.

The controller 18 is, for example, a personal computer. The controller 18 includes an imaging control unit 181 for controlling an imaging operation, an image synthesis unit 182 for performing image processing for an acquired image and generating a three-dimensional luminescence image, an imaging condition determination unit 183 for determining imaging conditions, and a storage unit 184 for storing various data.

The imaging control unit 181 controls the exposure time for acquiring one image. The imaging control unit 181 also controls how the focus position adjusted by the objective optical system drive unit 16 should be moved in the Z-axis direction, namely, the imaging pitch is controlled. The imaging control unit 181 causes the imaging unit 15 to take a set of two-dimensional luminescence images, including a plurality of two-dimensional luminescence images taken in different focal planes. The imaging control unit 181 controls an imaging time interval, which is between the acquisition of a set of two-dimensional luminescence images and the acquisition of another set of two-dimensional luminescence images.

The image synthesis unit 182 generates a three-dimensional luminescence image by combining a set of two-dimensional luminescence images together. Three-dimensional reconstruction processing, which is three-dimensional synthesis, is performed for generating a three-dimensional luminescence image. To be specific, the image synthesis unit 182 generates a three-dimensional luminescence image by arranging a set of two-dimensional luminescence images three-dimensionally and synthesizing them, using the position information on the respective images.

The imaging condition determination unit 183 determines imaging conditions controlled by the imaging control unit 181. To be specific, the imaging condition determination unit 183 determines, for example, an imaging time interval, an imaging pitch and an exposure time.

The storage unit 184 stores information required for the controller 18 to operate. This information includes programs under which the respective portions of the controller 18 operate. The storage unit 184 stores two-dimensional images obtained by imaging and three-dimensional luminescence images obtained by synthesis.

As described above, the imaging system 10 of the present embodiment acquires a plurality of three-dimensional luminescence images at predetermined imaging time intervals. In other words, the imaging system 10 performs time-lapse imaging of three-dimensional luminescence images.

The controller 18 incorporates an integrated circuit such as a central processing unit (CPU), an application specific integrated circuit (ASIC), a field programmable gate array (FPGA), or the like, and performs various operations. Each of the imaging control unit 181, image synthesis unit 182 and imaging condition determination unit 183 may be constituted by a single integrated circuit or by a combination of a number of integrated circuits. Two or more of the imaging control unit 181, image synthesis unit 182 and imaging condition determination unit 183 may be constituted by a single integrated circuit or the like. The operation of the controller 18 is executed in accordance with a program stored in the storage unit 184 or a storage area of the integrated circuit. The controller 18 calculates a luminescence intensity of the luminescence of each pixel, based on the two-dimensional images and/or the three-dimensional images stored in the storage unit 184, and sends information on the luminescence intensity of the entire image or local image portions to the imaging condition determination unit 183.

The display 19 includes a general type of display device such as a liquid crystal display device. The display 19 displays, for example, a three-dimensional luminescence image generated by the image synthesis unit 182. The display 19 also displays a two-dimensional luminescence image, another image, and control information representing how the controller 18 controls the imaging system 10.

The input device 20 includes a general type of input device, such as a keyboard, a touch panel, a switch, a slider, or the like. The input device 20 receives instructions from the user and transmits them to the controller 18.

Figure 2:
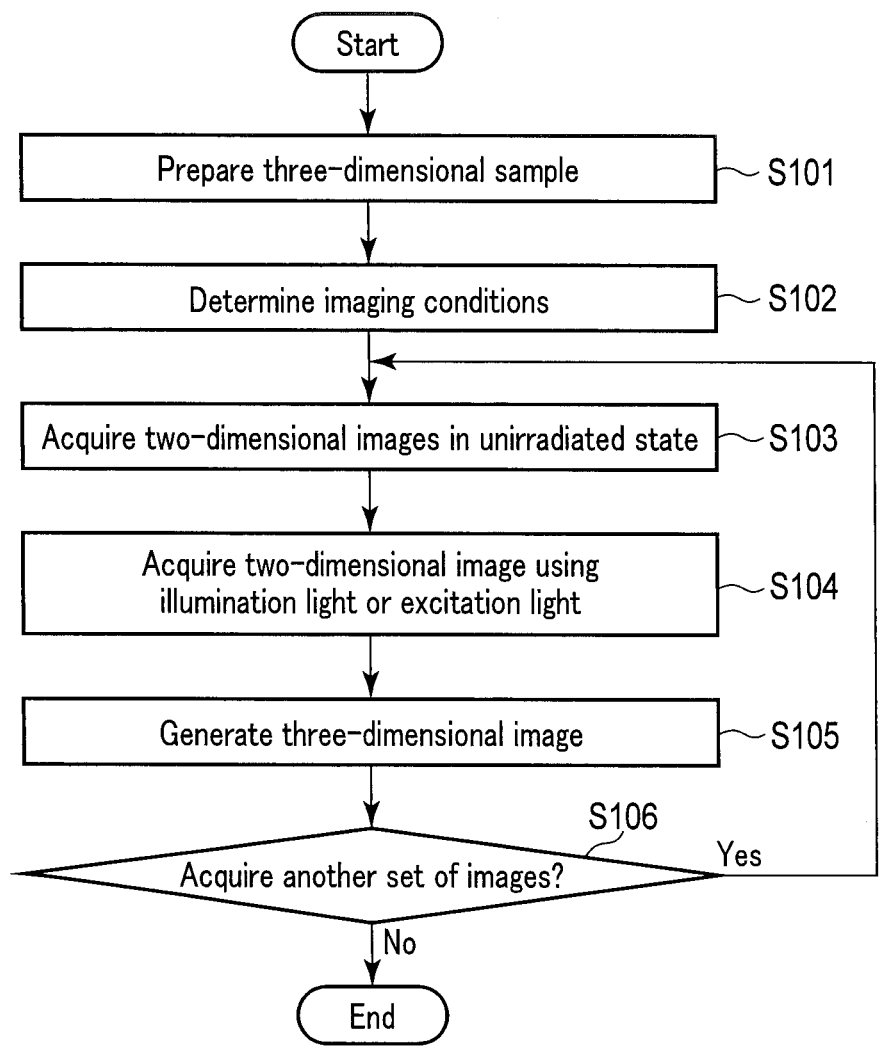
FIG. 2 is a flowchart illustrating an example of a three-dimensional luminescence image generation method according to the first embodiment of the present invention.

Next, the method for generating a three-dimensional luminescence image according to the present embodiment will be described with reference to the flowchart shown in FIG. 2.

In step S101, a three-dimensional sample is prepared. It should be noted that the three-dimensional sample contains a plurality of cells and has a three-dimensional shape. The three-dimensional sample includes, for example, an embryoid body or a spheroid derived from a stem cell, such as an iPS cell or ES cell, an aggregation or colony of various cells (such as cardiac muscle cells and nerve cells) into which the embryoid body or spheroid differentiates, or a number of stacked cell sheets. The three-dimensional sample is prepared to be self-luminescent, with no need for external excitation light. For example, cells of the three-dimensional sample are prepared to express luciferase and to be bioluminescent by the addition of luciferin. The three-dimensional sample is not limited to this. For example, the three-dimensional sample may be cells arranged on a carrier to be spaced from each other.

In step S102, imaging conditions are determined. The imaging conditions include imaging intervals, which are time intervals at which a set of two-dimensional luminescence images are acquired, an exposure time for acquiring one two-dimensional luminescence image, and an imaging pitch representing the distance by which the focus position of the objective optical system is moved in the optical axis direction and which corresponds to the interval between focal planes. In the first embodiment, the imaging conditions are determined as an optimal combination of them. For example, the imaging pitch can be determined based on the size and shape of the three-dimensional sample. The exposure time may be determined in accordance with the imaging pitch and the imaging time interval. Alternatively, the exposure time can be determined in accordance with the luminescence intensity of the three-dimensional sample. The imaging pitch may be determined in accordance with the exposure time and the imaging time interval.

In step S103, a plurality of two-dimensional luminescence images are acquired in an unirradiated state. These two-dimensional luminescence images are images of the luminescence produced by the three-dimensional sample. In this step, two-dimensional images having different focal planes are acquired as a set of two-dimensional images. A set of two-dimensional images may include two-dimensional images of all positions from one end to the other in the height direction of the three-dimensional sample; alternatively, they may include two-dimensional images of a particular region determined in the height direction of the three-dimensional sample.

In step S104, a two-dimensional transmission image may be acquired in an illuminated state using illumination light or excitation light. This transmission image may be used, for example, for determining imaging conditions. The transmission image may be used for generating a three-dimensional luminescence image described later. Where the transmission image is used for the generation of a three-dimensional luminescence image, not only information on the luminescence but also information representing how the information on the luminescence and the information on the transmission image are combined can be easily recognized.

In step S105, a three-dimensional luminescence image is generated based on a set of two-dimensional luminescence images acquired in step S103. The three-dimensional luminescence image can be generated by synthesizing the two-dimensional luminescence images based on the position information. When the three-dimensional luminescence image is generated, the transmission image taken under the illuminated condition and acquired in step S104 may be used.

In step S106, it is determined, after a given imaging time interval, whether another set of two-dimensional luminescence images are to be acquired and another three-dimensional luminescence image is to be generated based on them. If this is the case, steps S103 to S105 are repeated. In other words, time-lapse imaging for taking three-dimensional luminescence images is performed.

Figure 3:
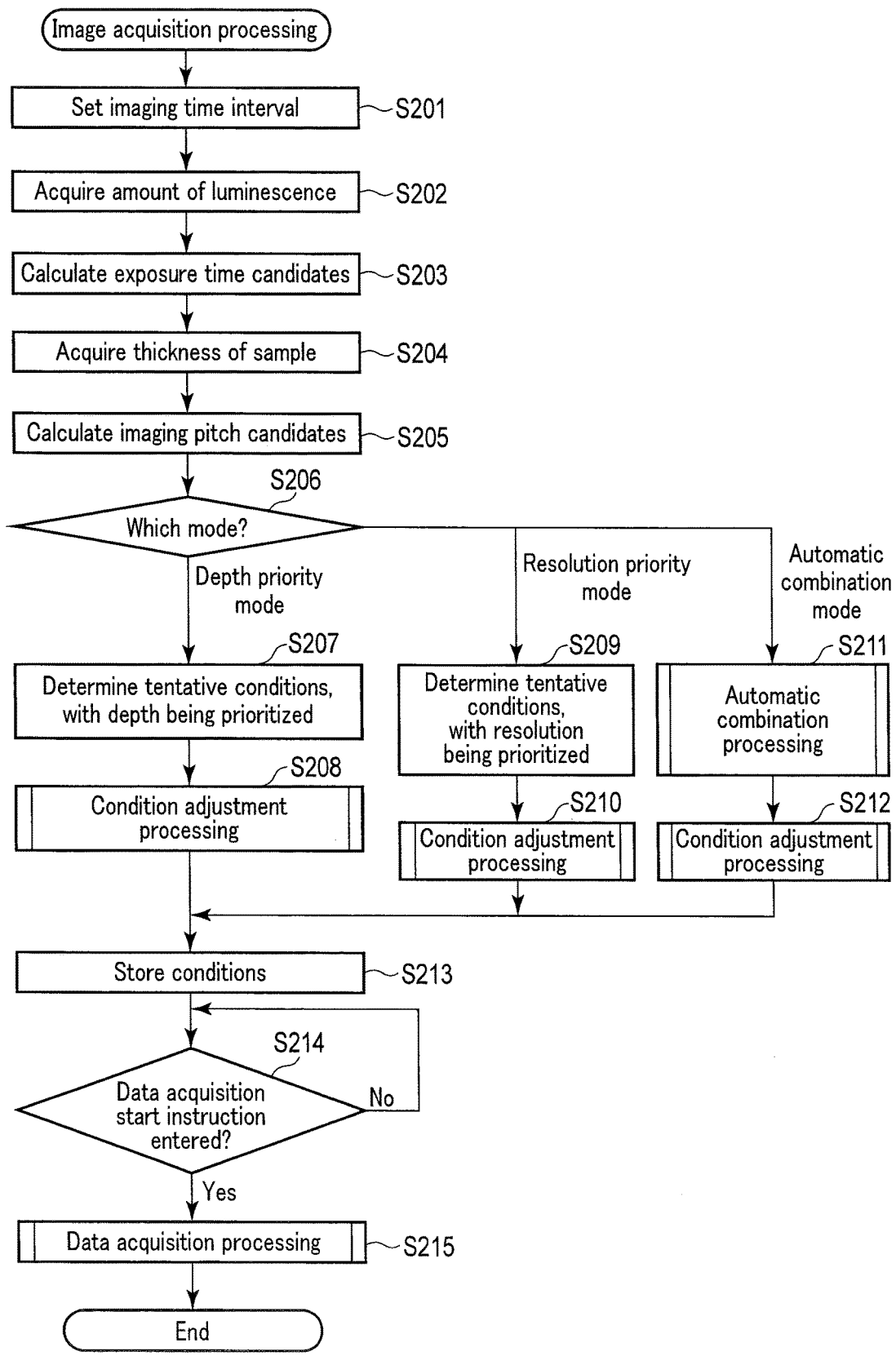
FIG. 3 is a flowchart illustrating an example of image acquisition processing according to the first embodiment of the present invention.

Next, a description will be given of how the imaging system 10 of the first embodiment performs image acquisition processing in which a three-dimensional luminescence image of a sample is acquired in a time-lapse manner. The image acquisition processing is started when the user enters a data acquisition start instruction from the input device 20 after setting a sample on the sample holder 11. The image acquisition processing will be described with reference to the flowchart shown in FIG. 3. This image acquisition processing is performed under the control of the controller 18.

In step S201, the controller 18 sets an imaging time interval based on the input which the user enters from the input device 20. The imaging time interval is determined, for example, in accordance with what experiment is to be performed. Where a phenomenon that changes in several seconds to several minutes is measured, as in the measurement of an intracellular calcium concentration, the imaging time interval should be short. On the other hand, where a phenomenon that changes gradually in several hours to several days is measured, as in the analysis of the differentiation of stem cells, the development investigation and the analysis of clock gene expression, the imaging time interval may be comparatively long.

In step S202, the controller 18 acquires the amount of luminescence as the brightness of the sample. For example, the controller 18 acquires a two-dimensional image of the sample and analyses the luminescence intensity of that image to acquire the amount of luminescence.

In step S203, the controller 18 calculates exposure time candidates based on the information obtained in step S202. The exposure times that are calculated as candidates should be exposure times that enable imaging. For example, in the case of 16-bit image data, a value from 0 to 65535 is used as a pixel value. For example, an exposure time that does not result in the saturation of a pixel value may be selected. An exposure time that permits the average value of the pixel values of all pixels to be 5000 or so may be selected as a value representing whether or not imaging can be performed. Thresholds may be determined with respect to an exposure time. The controller 18 considers the conditions for these exposure times and specifies an appropriate range of exposure times.

In step S204, the controller 18 acquires a thickness (depth) of the sample. To acquire the thickness of the sample, images of the sample are acquired, with the focus position being changed in the Z direction. Of the images thus obtained, the images corresponding to the upper and lower limits are specified, and the distance between the upper and lower limits is calculated. Desirably, the images acquired then should be bright field images taken under a light irradiated condition because they can be acquired reliably and in a short time. Luminescence images may be used in place of the bright field images.

In step S205, the controller 18 calculates imaging pitch candidates based on the sample thickness obtained in step S204.

In step S206, the controller 18 selects which mode should be used to determine imaging conditions. In the present embodiment, a depth priority mode, a resolution priority mode and an automatic combination mode are available. The user selects one of these modes. The controller 18 acquires an input entered from the input device 20 and specifies which mode is selected.

If the depth priority mode is selected in step S206, the processing advances to step S207. In step S207, the controller 18 determines tentative conditions for image acquisition, with the depth being prioritized. To be more specific, in the depth priority mode, the imaging pitch is narrowed, and data having a high resolution in the depth direction is acquired. For example, consideration will be given to the case where an imaging time interval of 30 minutes is selected with respect to a 100 μm-thick sample and at least one minute is required as an exposure time. Where the exposure time is one minute, 30 images can be acquired at focal intervals of 3.3 μm during the imaging time interval of 30 minutes. In this case, therefore, tentative conditions are determined such that the exposure time is one minute and the imaging pitch is 3.3 μm. After the tentative conditions for image acquisition are determined, the processing advances to step S208. The imaging pitch selected in the depth priority mode enables a single cell to be imaged at least twice. As can be seen from this, where a single cell should be imaged n times, an imaging pitch can be determined by dividing the average diameter m (μm) of target cells with n and subtracting a value (μm) that is not less than 0.1 and not more than (m−0.1) from the quotient (m/n). In order to image a single cell in the depth priority mode where the average diameter is 6 μm, the number of times the single cell is imaged can be changed from twice to four times by changing the imaging pitch from 1.4 μm to 2.9 μm. Likewise, where the average diameter of target cells is 10 μm, the imaging pitch can be selected from the range of 2.4 to 4.9 μm.

Figure 4:
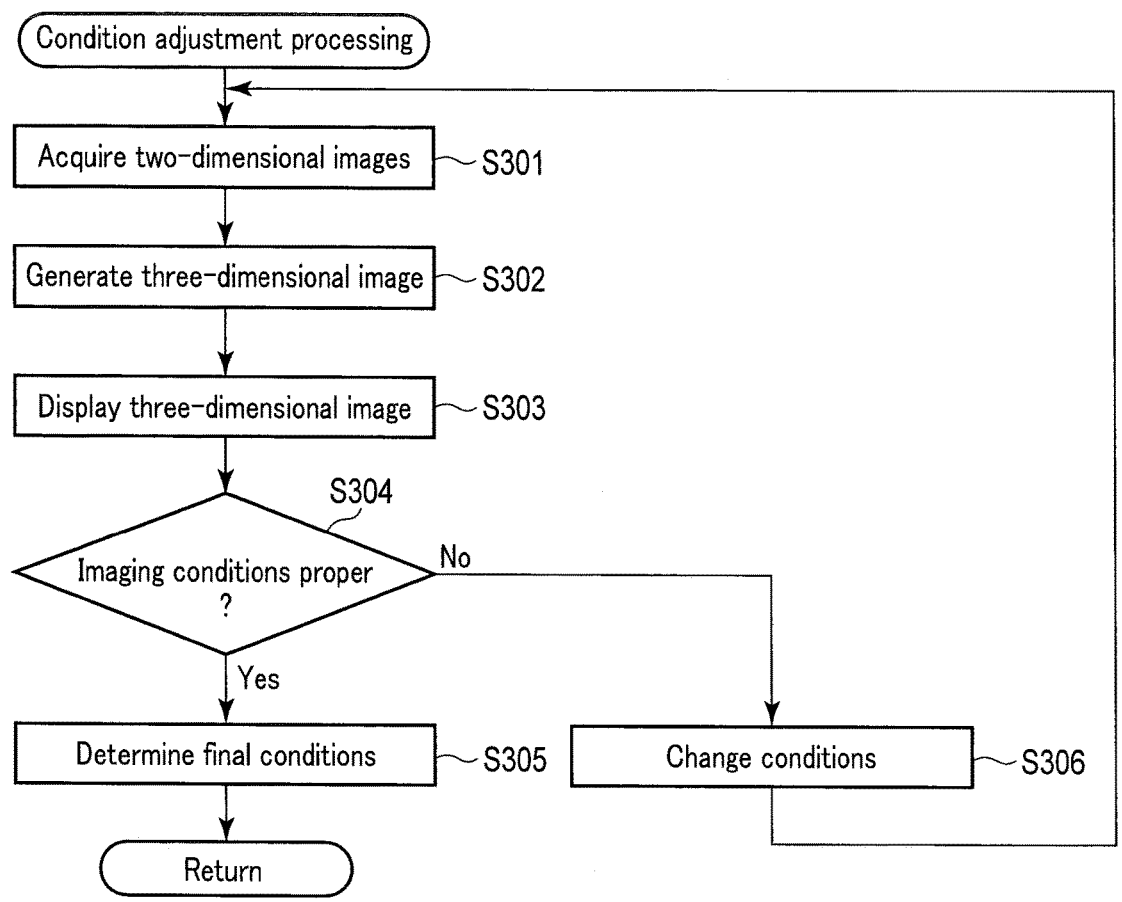
FIG. 4 is a flowchart illustrating an example of condition adjustment processing according to the first embodiment of the present invention.

In step S208, the controller 18 performs condition adjustment processing. The condition adjustment processing will be described with reference to the flowchart shown in FIG. 4.

In step S301, the controller 18 acquires a plurality of two-dimensional images, which are used for generating a three-dimensional luminescence image, under the determined tentative conditions for image acquisition, namely, the exposure time and the imaging pitch. For example, a two-dimensional image is acquired based on a given focus position and for a predetermined exposure time. Subsequently, the focus position is changed by the determined imaging pitch, and another two-dimensional image is acquired for the predetermined exposure time. This imaging operation is repeated.

In step S302, the controller 18 generates a three-dimensional luminescence image based on the images acquired in step S301. At the time, the images acquired in step S301 are subjected to deconvolution processing to cancel image blurring. The three-dimensional luminescence image is generated using the images subjected to the deconvolution processing.

In step S303, the controller 18 displays the generated three-dimensional luminescence image on the display 19.

In step S304, the controller 18 acquires the user's judgment as to whether or not the imaging conditions are proper. For example, current settings of the exposure time, imaging pitch and imaging time interval and icons for changing the current settings are displayed on the display 19. The user can enter his or her judgment result by selecting an icon. Where information indicating that the imaging conditions are proper is acquired, the processing advances to step S305.

In step S305, the controller 18 determines that the currently-set tentative conditions for image acquisition should be used as final conditions for image acquisition. Thereafter, the condition adjustment processing ends, and the processing returns to the image acquisition processing described with reference to FIG. 3.

If information indicating that the imaging conditions are improper is acquired in step S304, the processing advances to step S306. In step S306, the controller 18 acquires, from the user, changed values of the exposure time, imaging pitch and imaging time interval so as to change the conditions. There may be a case where, in relation to the imaging time interval, the imaging pitch has to be increased in accordance with an increase of the exposure time. In such a case, when the increase of the exposure time is entered, an imaging pitch corresponding to this change is calculated and displayed, or the change of the imaging time interval is displayed. After the conditions for image acquisition are determined again, the processing advances to step S301. Thereafter, two-dimensional images are acquired and a three-dimensional luminescence image is generated, under the newly-set conditions.

Turning back to FIG. 3, a description will be continued. After the condition adjustment processing is performed in step S208, the processing advances to step S213.

If the resolution priority mode is selected in step S206, the processing advances to step S209. In step S209, the controller 18 determines tentative conditions for image acquisition, with the resolution being prioritized. That is, in the resolution priority mode, the exposure time is increased to acquire a luminescence image having a high S/N ratio. For example, consideration will be given to the case where an imaging time interval of 30 minutes is selected with respect to a 100 μm-thick test sample, and four minutes are set as an exposure time to acquire a high-resolution image. Where the exposure time is four minutes, 7 images can be acquired at focal intervals of 14.3 μm during the imaging time interval of 30 minutes. In this case, tentative conditions are determined such that the exposure time is four minutes and the imaging pitch is 14.3 μm. After the tentative conditions for image acquisition are determined, the processing advances to step S210. The imaging pitch selected in the resolution priority mode is a dimension that enables imaging of one of two or more cells adjacent in the depth direction. As can be seen from this, where n (two or more) cells should be imaged once, an imaging pitch can be determined by multiplying the average diameter m (μm) of target cells by n and subtracting a value (μm) that is not less than 0.1 and less than one half of mn (mn/2) from the product (mn). In order to image a single cell in the resolution priority mode where the average diameter is 6 μm, imaging can be performed once for two to fourth cells by changing the imaging pitch from 6.1 μm to 23.9 μm. Likewise, where the average diameter is 10 μm, the imaging pitch can be selected from the range of 10.1 to 39.9 μm.

In step S210, the controller 18 performs condition adjustment processing. The condition adjustment processing is similar to the condition adjustment processing of step S208 described with reference to FIG. 4. After the condition adjustment processing, the processing advances to step S213.

Figure 5:
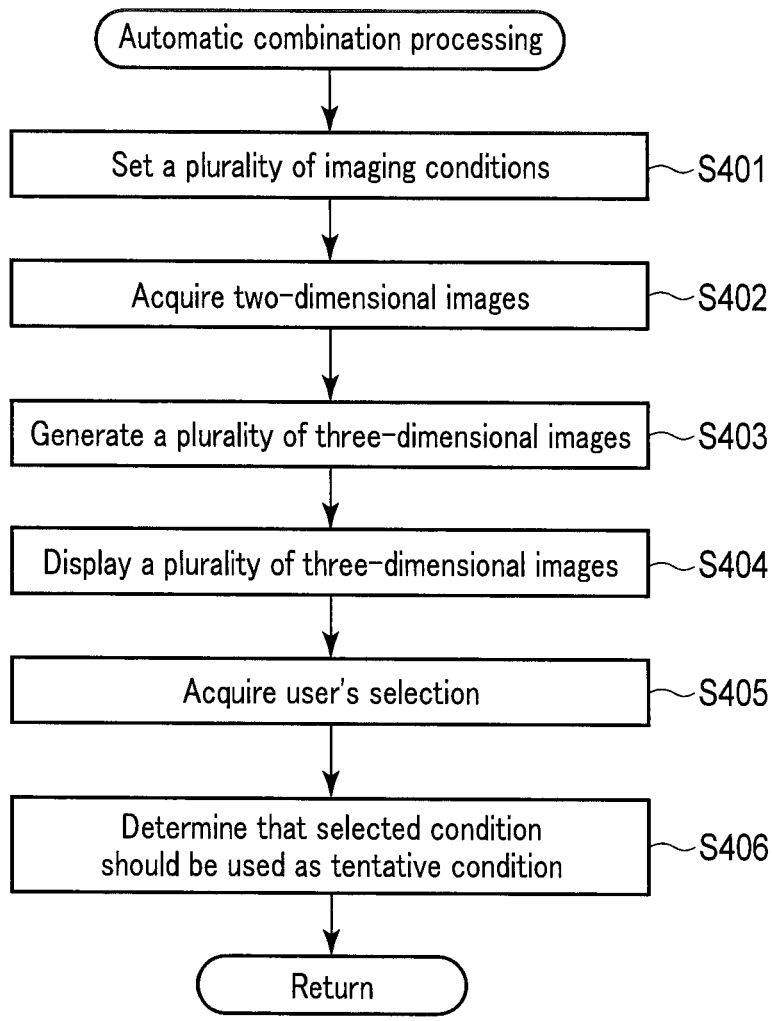
FIG. 5 is a flowchart illustrating an example of automatic combination processing according to the first embodiment of the present invention.

If the automatic combination mode is selected in step S206, the processing advances to step S211. In step S211, the controller 18 performs automatic combination processing. The automatic combination processing will be described with reference to the flowchart shown in FIG. 5.

In step S401, the controller 18 sets a plurality of imaging conditions, based on the imaging time interval acquired in step S201, the exposure time candidate acquired in step S203 and the imaging pitch candidate acquired in step S205.

In step S402, the controller 18 acquires a plurality of necessary two-dimensional images under the conditions set in step S401.

In step S403, the controller 18 generates a plurality of three-dimensional luminescence images, based on the two-dimensional images acquired in step S402.

In step S404, the controller 18 causes the display 19 to show a plurality of three-dimensional luminescence images generated in step S403, the imaging conditions under which the three-dimensional luminescence images are generated, etc. The user confirms the three-dimensional luminescence images, imaging conditions etc. shown on the display 19 and selects a desirable imaging condition.

In step S405, the controller 18 acquires which imaging condition is selected by the user. In step S406, the controller 18 determines that the condition acquired in step 405 should be used as a tentative condition. Thereafter, the automatic combination processing ends, and the processing returns to the image acquisition processing described with reference to FIG. 3.

Turning back to FIG. 3, a description will be continued. In step S212, the controller 18 performs condition adjustment processing. Subsequently, the processing advances to step S213. In step S213, the controller 18 stores the image acquisition conditions determined in the condition adjustment processing in the storage unit 184. In step S214, the controller 18 determines whether or not a data acquisition start instruction is entered. If the data acquisition start instruction is not entered, the processing returns to step S214, and entry of a data acquisition start instruction is waited for. If the image acquisition start instruction is entered, the processing advances to step S215.

In step S215, the controller 18 performs data acquisition processing. In the data acquisition processing, data is acquired in accordance with the determined image acquisition condition. That is, a luminescence image is acquired based on the determined exposure time. The focus position of this image is changed in accordance with the determined imaging pitch, thereby acquiring a plurality of luminescence images different in focus positions. Based on these luminescence images, a three-dimensional luminescence image is generated. A three-dimensional luminescence image, obtained in this manner, is acquired at imaging time intervals. In this manner, the processing ends.

The imaging conditions, including an imaging time interval, an exposure time and an imaging pitch, need not be constant throughout the measurement. For example, the depth may be prioritized in the early period of the observation, while the resolution may be prioritized in the latter period of the observation. In addition, the imaging time interval may be different between the early period of the observation and the latter period thereof.

Cell distribution information representing how cells are distributed inside an object to be imaged may be obtained from a transmission image. After the cell distribution in the height direction is confirmed, the position of an intermediate portion of the sample may be determined. In this manner, one three-dimensional luminescence image can be acquired in a minimal time when an image of bioluminescence requiring a long exposure time is acquired. As a result, efficient analysis is achieved.

A three-dimensional luminescence image acquired according to the embodiment is an image of the luminescence of a three-dimensional sample. By employing an observation method of the present embodiment, which utilizes the luminescence phenomenon, problems in the fluorescent observation resulting from autofluorescence do not occur. There may be a case where damage to a three-dimensional image by excitation light is not negligible in fluorescent observation. By employing an observation method of the present embodiment, which utilizes the luminescence phenomenon, problems in the fluorescent observation resulting from excitation light do not occur. Accordingly, the observation according to the present embodiment is applicable to long-term observation.

According to the present embodiment, the imaging time interval, exposure time and imaging pitch can be optimally determined in accordance with the purpose of an experiment and a sample to be observed.

For example, when an embryoid body or spheroid widely used in regenerative medicine is observed, three-dimensional images of not only the end portions as viewed in the height direction but also the intermediate portions are acquired, and how the gene expression takes place in the entire structure can be observed in three dimensions. The intermediate portions are closely related to the state of a living body, and the acquisition of data of such portions is significant. By acquiring three-dimensional luminescence images described above, images that enable comparison (or collation) of the internal structure of three-dimensional samples can be obtained.

Where the imaging pitch is determined based on the size and shape of an embryoid body or spheroid, a three-dimensional luminescence image can be acquired in consideration of the number of cells included in an imaging range and the density of the cells. In general, the average diameter of embryoid bodies or spheroids derived from stem cells is in the range of 50 μm to 1000 μm throughout the whole length. Where the whole length is of large value (e.g., 500 μm or more), it is preferable to select the resolution priority mode, in which the imaging pitch is increased and imaging is executed by a proper number of times. When a narrow region including intermediate portions which are largest in cross plane is imaged (the narrow region is a region having a depth corresponding to ⅓ to ⅕ of the whole length), it is preferable to select the depth priority mode in which only the narrow region is imaged with high accuracy. Since the imaging conditions can be properly changed, they can be determined in such a manner as to enable 3D observation with such accuracy as is required in the process of differentiation. Since a plurality of luminescence images are taken, with the focus position being changed in the optical axis direction, a three-dimensional sample, which is an object to be imaged, does not have to be moved or rotated.

Where the observation method according to the present embodiment is applied to the research made to understand the induction mechanism of the differentiation of stem cells, useful information can be obtained. For example, the method can be used for an analysis tool used for evaluating differentiation efficiency or for evaluating a differentiation induction reagent. In addition, where 3D luminescence observation is performed for embryoid bodies widely used in the research of regenerative medicine, highly-accurate analysis can be performed in due consideration of the height and thickness information, which cannot be obtained in a plane.

EXAMPLES

Example 1

A description will be given of three-dimensional luminescence observation of how cardiac muscle-specific marker expression takes place in the cardiac muscle induction process of iPS cells.

Cardiac troponin T (cTnT) is a protein which expresses specifically in the cardiac muscle. cTnT is utilized as marker genes for myocardial differentiation. An experimental system was prepared that enabled cTnT expression changes in the myocardial differentiation process of the embryoid body formation of mouse iPS cells to be analyzed as luminescence intensities. Three-dimensional observation was performed for embryoid bodies of the mouse iPS cells.

Experimental Method (1) Production of Mouse iPS Cells into which Nucleic Acid Including Promoter Region of cTnT Genes and Luciferase Genes was Introduced The promoter region for cTnT genes was inserted into a neomycin-resistant pGL4.17 luciferase reporter vector (Promega) to construct a "cTnT gene expression specific luminescent vector pcTnT-GL4."

The KO DMEM culture medium was used to culture mouse iPS cells (iPS-MEF-Ng-20D-17, Kyoto University) into which the vector was to be introduced. These iPS cells were cultured on MEF cells whose division was arrested by a mitomycin C treatment.

A Nucleofection method was used to transfect the pcTnT-GL4 gene expression vector into the mouse iPS cells. The transfected cells were cultured overnight in the KO DMEM culture medium together with neomycin-resistant feeder cells. Thereafter, the culture medium was replaced with KO DMEM culture medium to which the antibiotic G418 (Invitrogen) was added to a final concentration of 250 µg/ml, whereby a selective culture was conducted. In this way, a stably expressing cell line was acquired. These cells will be hereinafter referred to as cTnT-GL4 expression mouse iPS cells.

(2) Formation of Embryoid Body of cTnT-GL4 Expression Mouse iPS Cells

The cultured cTnT-GL4 expression mouse iPS cells were washed with PBS, detached by 0.25% Trypsin-EDTA, and then incubated for 4 hours in an incubator at 37° C. with the KO DMEM culture medium. Feeder cells (MEF) were adhered so that the mouse iPS cells floated alone. The culture medium including the mouse iPS cells was centrifuged to collect the cells, and the cells were resuspended in 1 ml of KO DMEM culture medium or IMDM culture medium. The number of cells in the solution was measured by a cell counter, and a cell suspension was added so that the number of cells was 2500 or 5000 in each well with Lipidure-Coat culture medium (96 Well Round Bottom; NOF Cooperation) to which the IMDM culture medium was added. The cells were cultured at 37° C. for 3 to 7 days to form an embryoid body.

(3) Myocardial Differentiation Induction of cTnT-GL4 Expression Mouse iPS Cells

The formed embryoid body was moved to a gelatin-coated 35 mm dish, and incubated overnight at 37° C. so that the embryoid body adhered to the dish surface. The embryoid body was cultured at 37° C. for 5 to 14 days to induce its differentiation into beating cardiac muscle cells.

(4) Observation and Analysis of cTnT-GL4 Expression Mouse iPS Cells

D-luciferin (Wako Pure Chemical Industries) was added to a final concentration of 1 mM to the embryoid body of the cTnT-GL4 expression mouse iPS cells which were cultured at 37° C. and came to partly show beating cardiac muscle. The beating cells were observed by three-dimensional luminescence observation by use of the bioluminescence microscope LV200 (Olympus Corporation) equipped with analysis software celiSens (by Olympus Corporation). The imaging conditions were that the objective lens had a magnifying power of 20, the CCD camera was ImagEM (Hamamatsu Photonics Corporation), and the binning was 1×1.

The exposure time at each focus position was 3 minutes, 5 minutes or 10 minutes. The imaging pitch was 10 µm, 50 µm or 100 µm.

Experimental Results and Discussion

Figure 6:
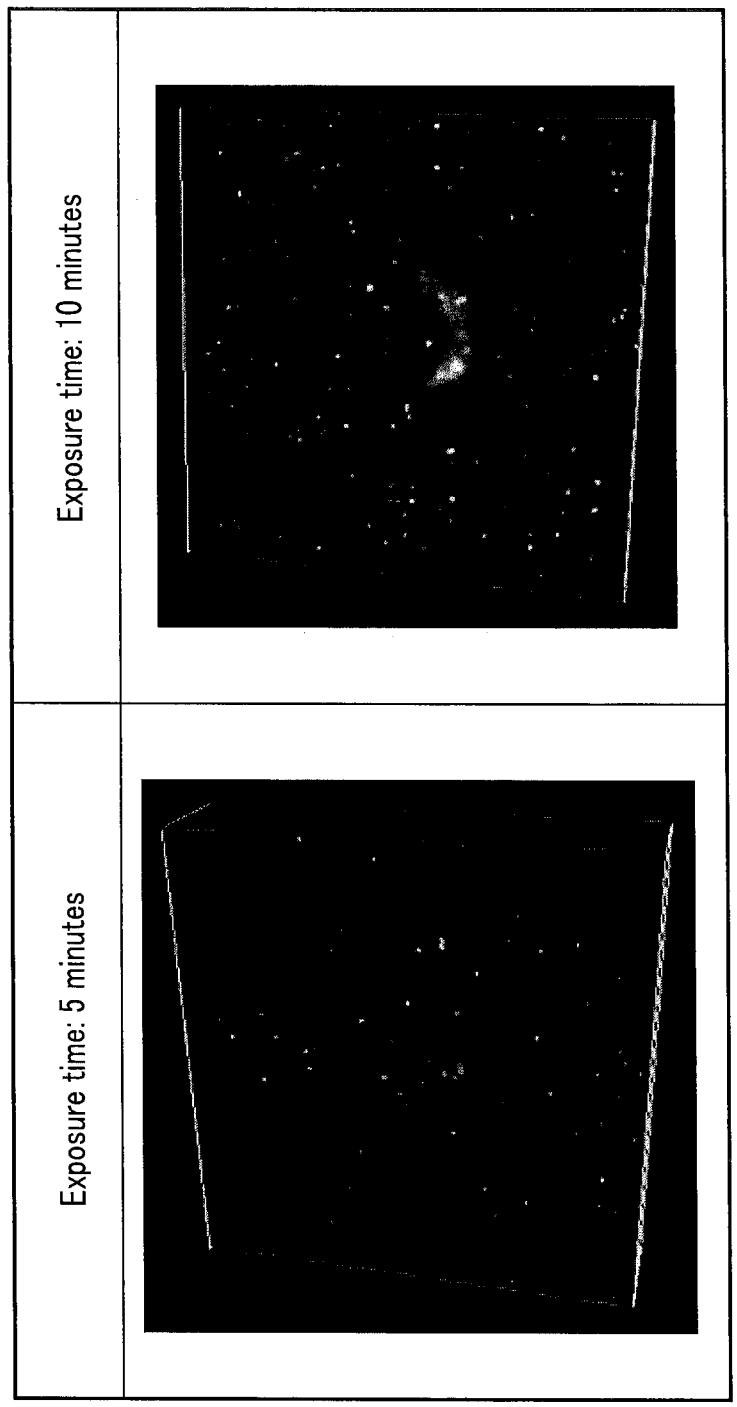
FIG. 6 shows examples of three-dimensional luminescence images acquired according to one embodiment of the present invention.

FIG. 6 shows imaging results obtained when 20 images were acquired, with the focus position being changed at an imaging pitch of 10 µm (total: 1000 µm). In FIG. 6, the image on the left side is a three-dimensional reconstruction image obtained from two-dimensional images acquired for an exposure time of 5 minutes, while the image on the right side is a three-dimensional reconstruction image obtained from two-dimensional images acquired for an exposure time of 10 minutes.

As can be seen from FIG. 6, in the present experiment system, the exposure is excessive when the exposure time is 10 minutes, and the resolution is better when the exposure time is 5 minutes.

Figure 7:
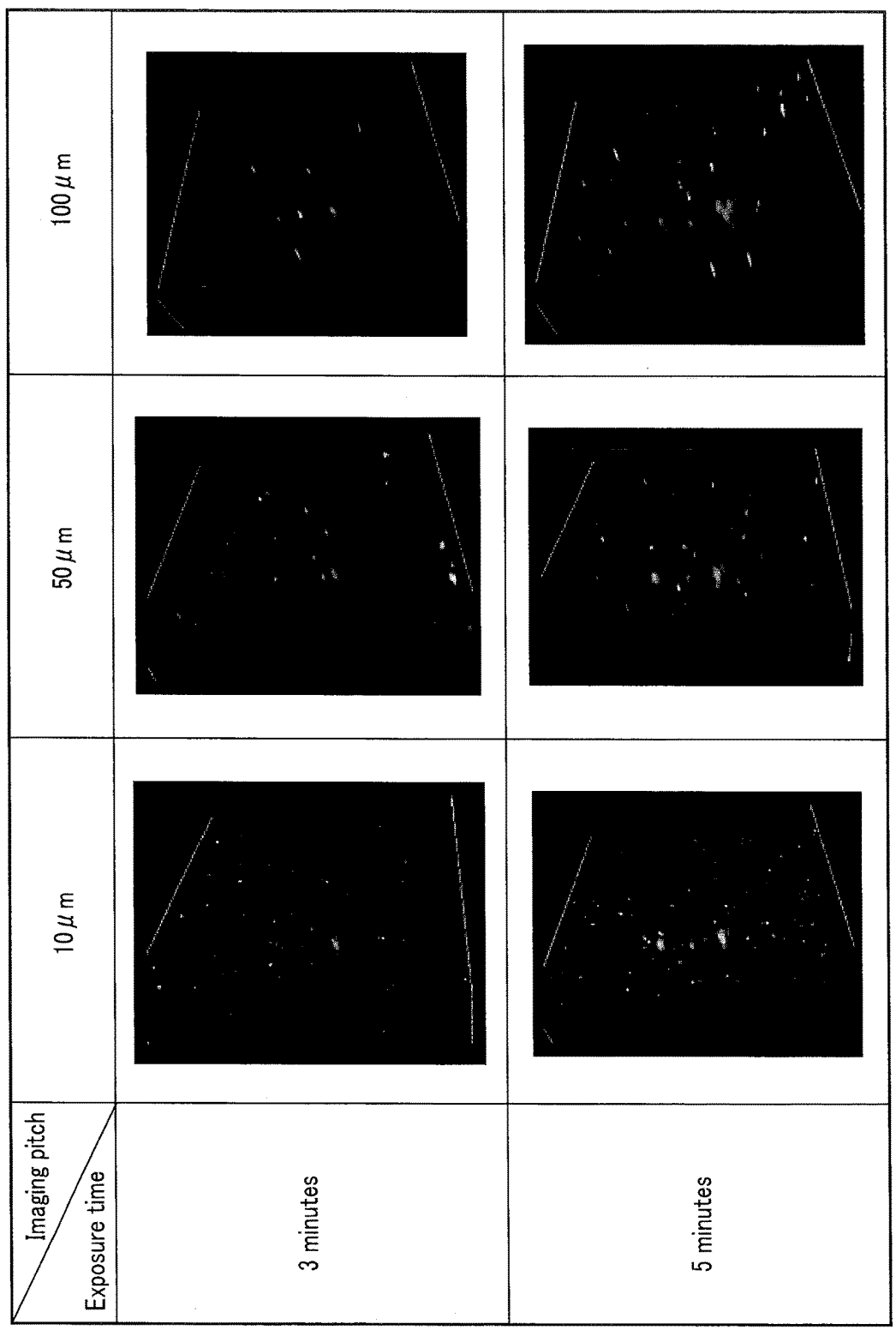
FIG. 7 shows examples of three-dimensional luminescence images acquired according to one embodiment of the present invention.

FIG. 7 shows results obtained when a 400 µm-thick region was imaged, with the exposure time set at 3 minutes or 5 minutes and the imaging pitch set at 10 µm, 50 µm or 100 µm. In FIG. 7, the images on the upper side show the case where two-dimensional images are acquired for an exposure time of 3 minutes, while the images on the lower side show the case where two-dimensional images are acquired for an exposure time of 5 minutes. In FIG. 7, the images in the left column show the case where a three-dimensional luminescence image was reconstructed from 40 images acquired with an imaging pitch of 10 µm. The images in the middle column show the case where a three-dimensional luminescence image was reconstructed from 8 images acquired with an imaging pitch of 50 µm. The images in the right column show the case where a three-dimensional luminescence image was reconstructed from 4 images acquired with an imaging pitch of 100 µm.

As can be seen from FIG. 7, the experiment system provides a better resolution when the exposure time is 5 minutes than when the exposure time is 3 minutes. The experiment system provides a high spatial resolution when the imaging pitch is short. As can be seen from the above, various three-dimensional images can be acquired by selectively using the depth priority mode and the resolution priority mode. Where a three-dimensional luminescence image is taken in different imaging modes, that internal portion of a three-dimensional sample in which the gene expression changes greatly can be imaged in the depth priority mode. By so doing, more information can be obtained in a short time. Even if the gene expression changes greatly in partial portions, such changes can be accurately observed.

Figure 8:
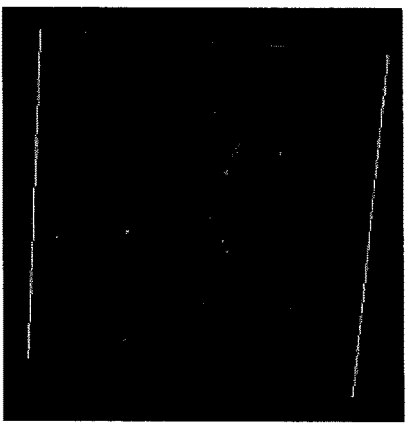
FIG. 8 shows examples of three-dimensional luminescence images acquired according to one embodiment of the present invention.

FIG. 8 shows results obtained when a 400 µm-thick region was imaged, with the exposure time set at 3 minutes or 5 minutes and the imaging pitch set at 10 µm or 100 µm. In FIG. 8, the images on the upper side show the case where two-dimensional images are acquired for an exposure time of 3 minutes, while the images on the lower side show the case where two-dimensional images are acquired for an exposure time of 5 minutes. In FIG. 8, the images in the left column show the case where a three-dimensional luminescence image was reconstructed from 40 images acquired with an imaging pitch of 10 µm. The images in the right column show the case where a three-dimensional luminescence image was reconstructed from 4 images acquired with an imaging pitch of 100 µm.

As can be seen from FIG. 8, the experiment system provides a better resolution when the exposure time is 5 minutes than when the exposure time is 3 minutes. The experiment system provides a high spatial resolution when the imaging pitch is short.

As described above, different three-dimensional luminescence images can be obtained by changing imaging conditions. That is, it is important to properly select the imaging conditions.

A sample was irradiated with light of a predetermined wavelength emitted from a light source, and a transmission image was acquired using bright field illumination or fluorescence. By confirming the internal structure of a three-dimensional sample beforehand, an imaging range in the height direction of the sample could be properly designated. The three-dimensional information obtained from the apex of the three-dimensional sample or from the adhesion portion of the bottom face of a vessel may be physically affected by the gravity force or adsorption force and may become noise in the analysis of the expression. It was therefore important to select an intermediate portion as an imaging range since such a portion is little affected. Without reference to the culture stage, the selection of a proper imaging pitch was important to reliably analyze the cells in the sample where the number of cells or the density of the cells vary in accordance with the degree of differentiation inside the sample, as in an embryoid body or spheroid.

It was made clear that a three-dimensional luminescence image suited to the purpose of an experiment could be prepared by acquiring two-dimensional images under proper conditions and constructing a three-dimensional image based on the two-dimensional images.

Example 2

By performing time-lapse observation using the three-dimensional luminescence observation method, cTnT expression in the myocardial differentiation process of cTnT-GL4 mouse iPS cells can be observed in three dimensions and with time.

Second Embodiment

The second embodiment of the present invention will be described. In the description below, reference will be made to how the second embodiment differs from the first embodiment. Therefore, the same symbols will be used to denote structural elements similar or corresponding to those of the first embodiment, and a description of such structural elements will be omitted. In the second embodiment as well, time-lapse observation is performed, in which the acquisition of a three-dimensional image generated based on a plurality of two-dimensional images is repeated. The acquisition of the three-dimensional image is performed by repeating the same processing at constant intervals. The second embodiment is featured in that in the acquisition of a set of two-dimensional images used for acquiring a three-dimensional image, the imaging pitch (which is an interval by which one two-dimensional image and another two-dimensional image are away from each other in the Z-axis direction) is changed each time the three-dimensional image is acquired.

The Z-axis interval between two-dimensional images (namely, the imaging pitch) will be described with reference to the drawings. FIG. 9 is a schematic diagram illustrating how an image of a three-dimensional sample 300 is acquired. In FIG. 9, a first region of interest 301 and a second region of interest 302 are included inside the three-dimensional sample 300. For example, consideration will be given of the case where the three-dimensional sample 300 is observed, with the focus position of the objective lens 142 being changed. Focal planes in which images are acquired are indicated by the broken lines. That is, a two-dimensional image is acquired in each of a first focal plane 401, a second focal plane 402, a third focal plane 403, a fourth focal plane 404, a fifth focal plane 405 and a sixth focal plane 406. The range in which an image is obtained in accordance with the depth of focus of the objective optical system 14 is indicated by symbol "I" on the rightmost portion of FIG. 9. The height of "I" indicate the depth of focus, namely an in-focus range. To be specific, the image acquisition performed in the first focal plane 401 generates an image of a first range 411. Likewise, the image acquisitions performed in the second focal plane 402, third focal plane 403, fourth focal plane 404, fifth focal plane 405 and sixth focal plane 406 generate images of second range 412, third range 413, fourth range 414, fifth range 415 and sixth range 416, respectively.

As a result, the image schematically shown in FIG. 10 is obtained. That is, images of the first range 411, second range 412, third range 413, fourth range 414, fifth range 415 and sixth range 416 are obtained. On the other hand, images of the halftone portions in FIG. 10, namely, a first missing region 421 between the first range 411 and the second range 412, a second missing region 422 between the second range 412 and the third range 413, a third missing region 423 between the third range 413 and the fourth range 414, a fourth missing region 424 between the fourth range 414 and the fifth range 415, and a fifth missing region 425 between the fifth range 415 and the sixth range 416, are not obtained. In other words, a complete image of the three-dimensional sample 300, including the first region of interest 301 and the second region of interest 302, cannot be obtained.

Figure 11:
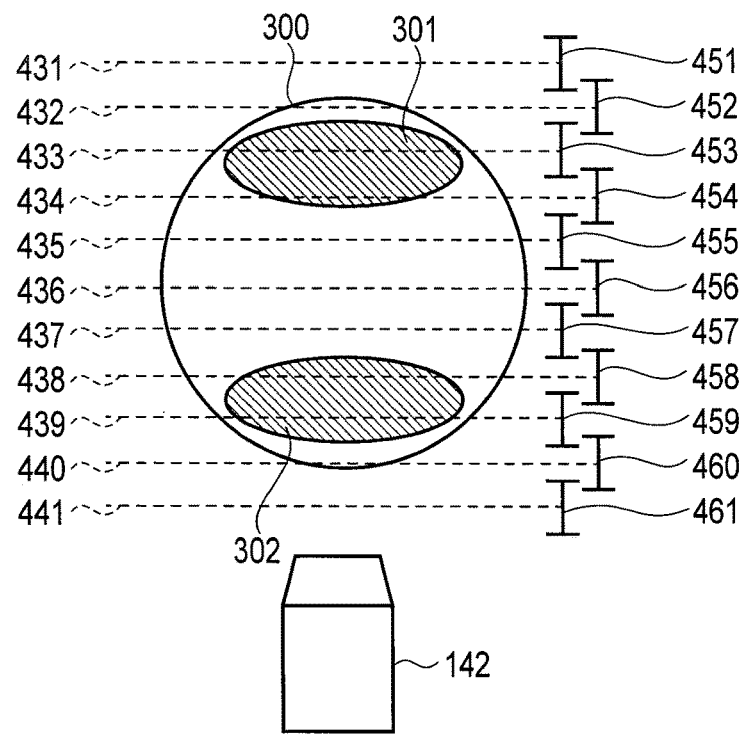
FIG. 11 is a schematic diagram for explaining how image acquisition of a three-dimensional sample is performed according to the second embodiment and showing the case where the interval between imaging planes is shorter than the depth of focus of an objective optical system.

FIG. 11 is a schematic diagram illustrating the case where the number of times imaging is performed is increased and the interval between the focus positions in which imaging is performed is shortened, as compared with the case shown in FIG. 9. As shown in FIG. 11, a two-dimensional image is acquired in each of a first focal plane 431, a second focal plane 432, a third focal plane 433, a fourth focal plane 434, a fifth focal plane 435, a sixth focal plane 436, a seventh focal plane 437, an eighth focal plane 438, a ninth focal plane 439, a tenth focal plane 440 and an eleventh focal plane 441. It should be noted that the focal interval between first focal plane 431 and second focal plane 432 (i.e., the focal interval shown in FIG. 11) is shorter than the focal interval between first focal plane 401 and second focal plane 402 (i.e., the focal interval shown in FIG. 9). As a result, no gap is present between the ranges in which images are obtained when the first focal plane 431, second focal plane 432, third focal plane 433, fourth focal plane 434, fifth focal plane 435, sixth focal plane 436, seventh focal plane 437, eighth focal plane 438, ninth focal plane 439, tenth focal plane 440 and eleventh focal plane 441 are in focus. That is, no gap is present between a first range 451, a second range 452, a third range 453, a fourth range 454, a fifth range 455, a sixth range 456, a seventh range 457, an eighth range 458, a ninth range 459, a tenth range 460 and an eleventh range 461. For example, the first range 451 and the second range 452 overlap each other.

Figure 12:
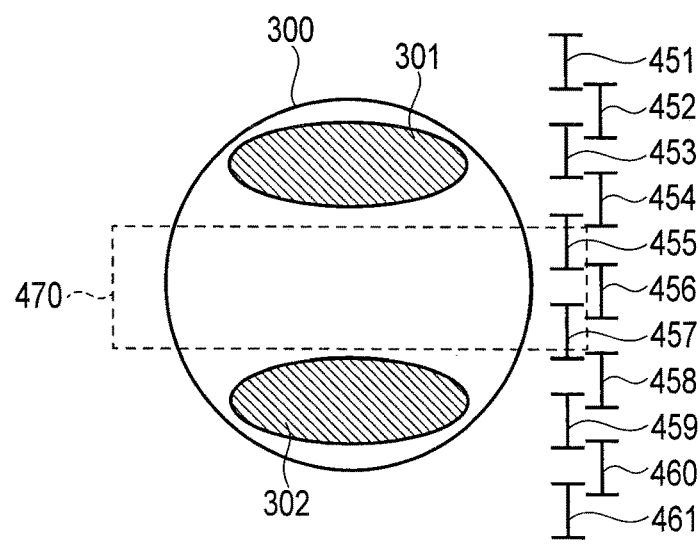
FIG. 12 is a schematic diagram for explaining a three-dimensional image obtained according to the second embodiment.

As a result, an image such as that shown in FIG. 12 is obtained. In other words, a complete image of the three-dimensional sample 300, including the first region of interest 301 and the second region of interest 302, can be obtained. Although mention was made of the case where the imaging ranges overlap each other, they do not have to overlap each other. They may be adjacent to each other, with no gap in between.

In the case of the three-dimensional image obtained under the condition where the interval between the focal planes is long, as shown in FIG. 10, the information is incomplete and the image is unclear. In this case, the number of two-dimensional images acquired is small, and the data size is small. On the other hand, in the case of the three-dimensional image obtained under the condition where the interval between the focal planes is short, as shown in FIG. 12, all information on an observation target is included, and the image is a high-resolution image. In this case, the number of two-dimensional images acquired is large, and the data size is large.

Figure 13:
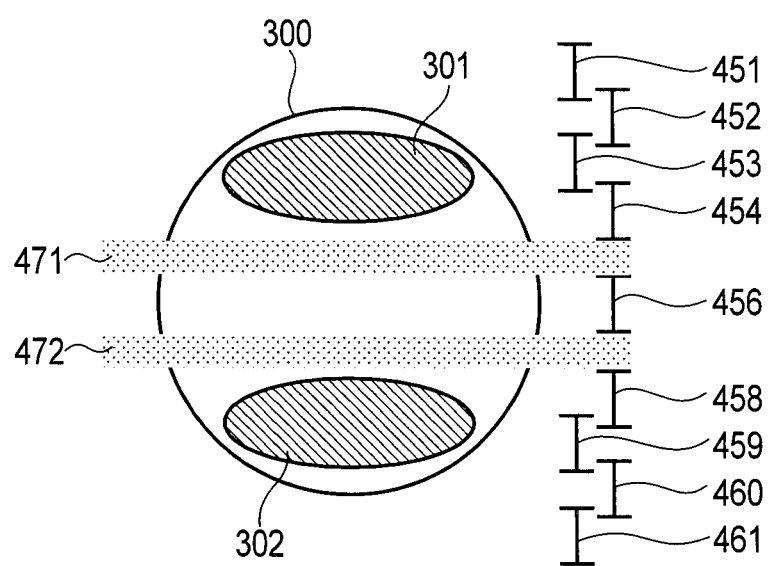
FIG. 13 is a schematic diagram for explaining a three-dimensional image obtained according to the second embodiment.

As indicated by the broken-line rectangle 470 in FIG. 12, the region which is neither the first region of interest 301 nor the second region of interest 302 does not have to be imaged with a high resolution. In the present embodiment, therefore, two-dimensional images for the fifth range 455 and seventh range 457 shown in FIG. 12 are not acquired. As shown in FIG. 13, the present embodiment generates first and second missing regions 471 and 472, but for the purpose of reducing the data size, acquires an image only for the following ranges: the first range 451, second range 452, third range 453, fourth range 454, sixth range 456, eighth range 458, ninth range 459, tenth range 460 and eleventh range 461.

Figure 14:
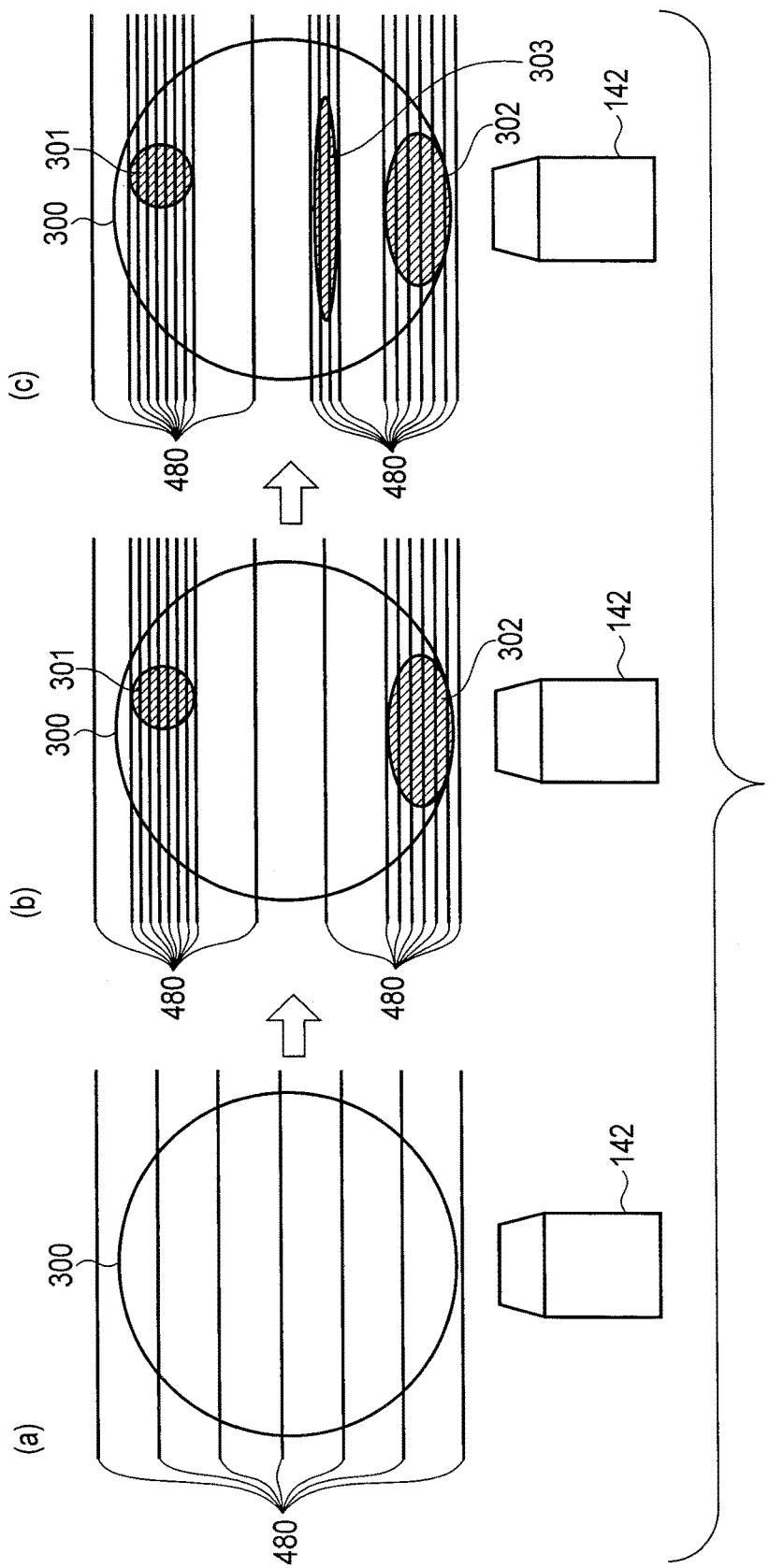
FIG. 14 is a schematic diagram for explaining the outline of the operation of an imaging system according to the second embodiment.

An operation of the imaging system 10 of the present embodiment will be briefly described with reference to FIG. 14. FIG. 14 illustrates how the focal plane used for imaging is changed with time. In FIG. 14, time passes in the order of the left diagram (a), the middle diagram (b) and the right diagram (c). In each of the diagrams, the horizontal lines 480 indicate focal planes in which imaging is performed. The focal planes in which imaging is performed will be hereinafter referred to as imaging planes 480.

Where the three-dimensional sample 300 does not include a region of interest from which luminescence is emitted, as shown in the left diagram (a) of FIG. 14, the focal interval between the imaging planes is set to be long throughout the entire three-dimensional sample 300. The focal interval between the imaging planes 480 is more than the depth of focus of the objective optical system 14.

If a first region of interest 301 and a second region of interest 302 are generated, as in the middle diagram (b) of FIG. 14, the regions including the first region of interest 301 and second region of interest 302 are detected. The focal interval between the imaging planes 480 is set to be short for the regions including the first region of interest 301 and the second region of interest 302, and is set to be long for the other regions. The focal interval between imaging planes 480 that is set to be short is equal to the depth of focus of the objective optical system 14 or less than the depth of focus of the objective optical system 14. In the description below, the focal interval equal to or less than the depth of focus will be referred to as a first interval, and the interval more than the depth of focus will be referred to a second interval.

If a third region of interest 303 is generated in addition to the first region of interest 301 and second region of interest 302, as in the right diagram (c) of FIG. 14, the regions including the first region of interest 301, second region of interest 303 and third region of interest 303 are detected. In the regions including the first region of interest 301, second region of interest 302 and third region of interest 303, the focal interval between imaging planes 480 is set at the first interval (i.e., a short interval), and in the other regions, the focal interval between imaging planes 480 is set at the second interval (i.e., a long interval). If a region of interest disappears, the focal interval between imaging planes 480 is changed from the first interval to the second interval for such a region. In this manner, in the present embodiment, the focal interval between imaging planes is properly changed in accordance with whether or not there is a region of interest from which luminescence is emitted.

The operation of the imaging system 10 of the second embodiment will be described with reference to a flowchart. FIG. 15 schematically illustrates an example of image acquisition processing according to the present embodiment.

In step S501, the controller 18 determines initial settings for image acquisition. The initial settings include, for example, the setting of an image acquisition region, which is a Z-axis direction range where an image is acquired, the setting of imaging timings, which include time intervals (imaging time intervals) at which an image is acquired by time-lapse imaging, etc.

In step S502, the imaging condition determination unit 183 of the controller 18 performs imaging plane setting processing. In the imaging plane setting processing, an imaging plane, i.e., a focal plane in which a two-dimensional image is acquired, is set in accordance with where in a three-dimensional sample luminescence is located. That is, the imaging condition determination unit 183 determines the interval between imaging planes. In this way, the imaging condition determination unit 183 functions as a focal interval setting unit when a plurality of two-dimensional images having mutually different focal planes are acquired, and the interval setting unit sets a focal interval between the two-dimensional images in accordance with the localization of luminescence in the three-dimensional sample. The imaging plane setting processing will be described with reference to the flowchart shown in FIG. 16.

In step S601, the imaging condition determination unit 183 analyzes the luminescence distribution of the two-dimensional image acquired last time in the imaging operation.

In step S602, the imaging condition determination unit 183 specifies how a region of interest is distributed three-dimensionally, based on the luminescence distribution obtained in step S601.

In step S603, the imaging condition determination unit 183 sets imaging planes in the image acquisition region in accordance with the distribution of the region of interest specified in step S602.

When the imaging plane setting processing is performed for the first time, there is no two-dimensional image (imaging result) obtained last time. Therefore, the imaging planes are set, for example, at the second intervals throughout the image acquisition region.

A description will be given of an example of a condition under which the interval between imaging planes is set at the first interval, which is equal to or less than the depth of focus of the objective optical system 14.

Figure 17:
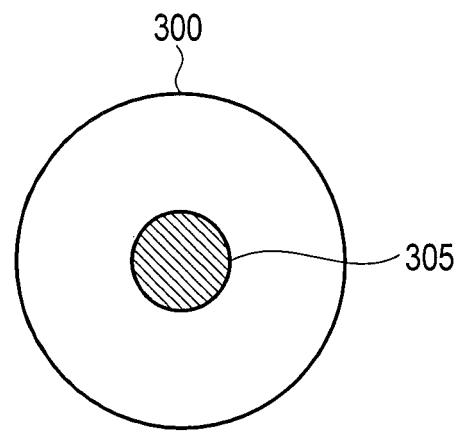
FIG. 17 is a schematic diagram for explaining a condition under which the interval between imaging planes is set to be short according to the second embodiment.

By way of example, let us consider the case where one large region 305 in an imaging plane emits luminescence, as shown in FIG. 17. If the luminescence intensity of the luminescence emission is higher than a threshold, a region having such a luminescence intensity is regarded as a high luminescence region. Where an area of the high luminescence region is larger than a predetermined threshold, the imaging system 10 may regard the imaging plane as including a region of interest and set the focal interval between imaging planes to be the first interval (which is equal to or less than the depth of focus of the objective optical system 14) in the neighborhood of the imaging plane.

Figure 18:
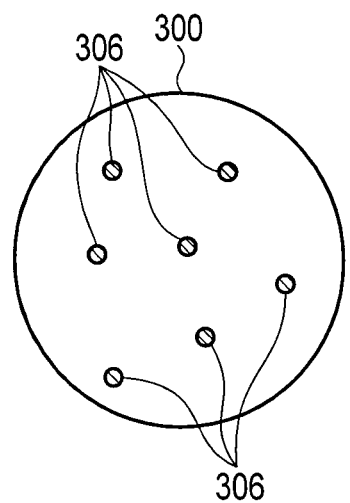
FIG. 18 is a schematic diagram for explaining a condition under which the interval between imaging planes is set to be short according to the second embodiment.

Alternatively, the imaging system 10 may be configured as follows. Let us consider the case where a number of small regions 306 in an imaging plane emit luminescence, as shown in FIG. 18. Of the luminescence intensity of the luminescence-emitting region 306, the highest luminescence intensity is regarded as a luminescence intensity of luminescence emission, and when the luminescence intensity of luminescence emission is larger than a threshold, the imaging plane is regarded as including a region of interest. That is, the imaging system 10 may set the focal interval between imaging planes to be the first interval (which is equal to or less than the depth of focus of the objective optical system 14) in the neighborhood of the imaging plane.

Alternatively, the imaging system 10 may be configured as follows. That is, where a certain region in an imaging plane is determined as a region of interest, and a change of the luminescence intensity in that region of interest is larger than a predetermined threshold, the imaging system 10 may regard the imaging plane as including a region of interest and set the focal interval between imaging planes to be the first interval (which is equal to or less than the depth of focus of the objective optical system 14) in the neighborhood of the imaging plane. Likewise, where a change of the luminescence intensity for the entire imaging plane is larger than a predetermined threshold, the focal interval between imaging planes may be set as the first interval.

Figure 19:
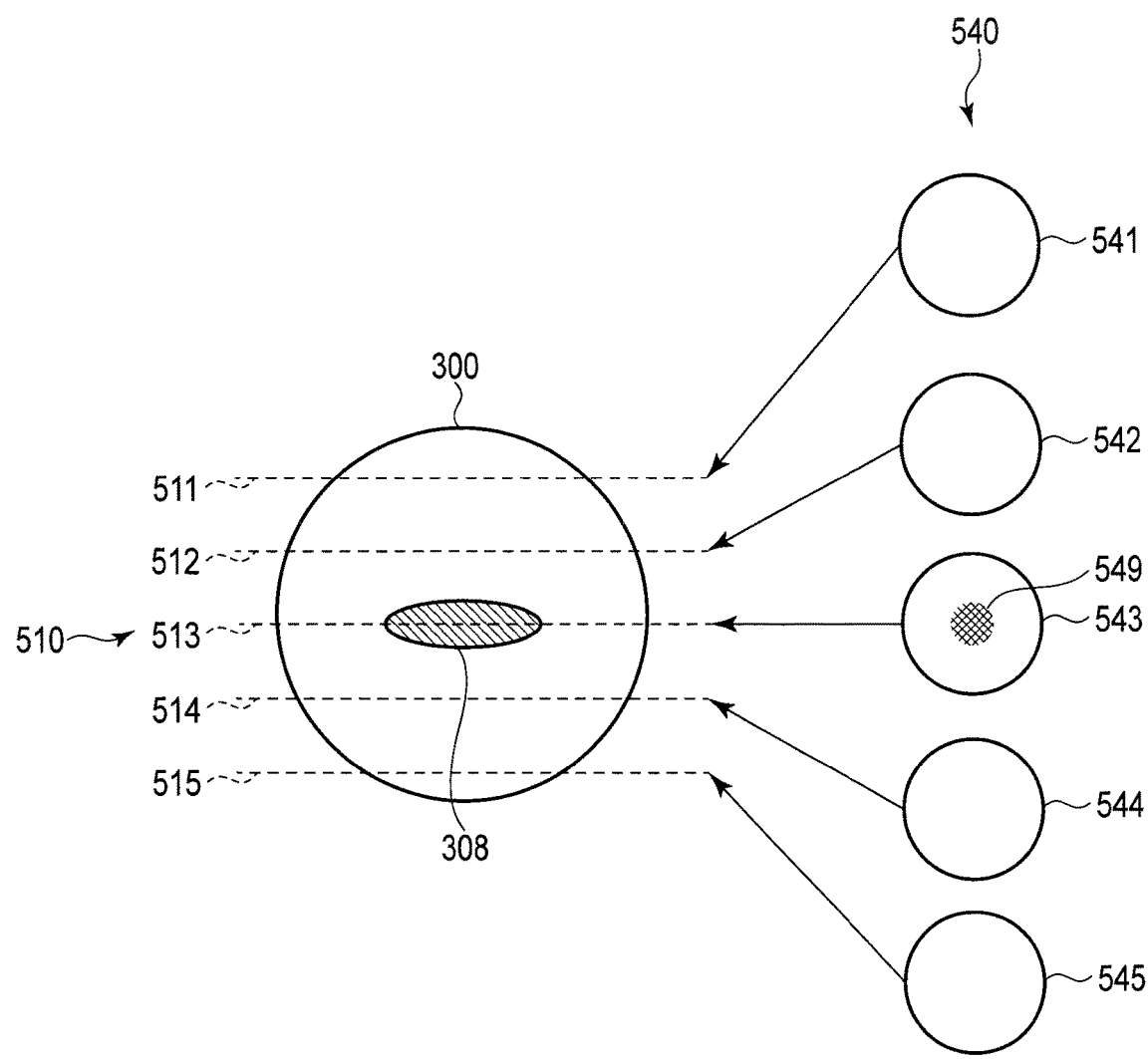
FIG. 19 is a schematic diagram for explaining how the interval between imaging planes is set according to the second embodiment.
Figure 20:
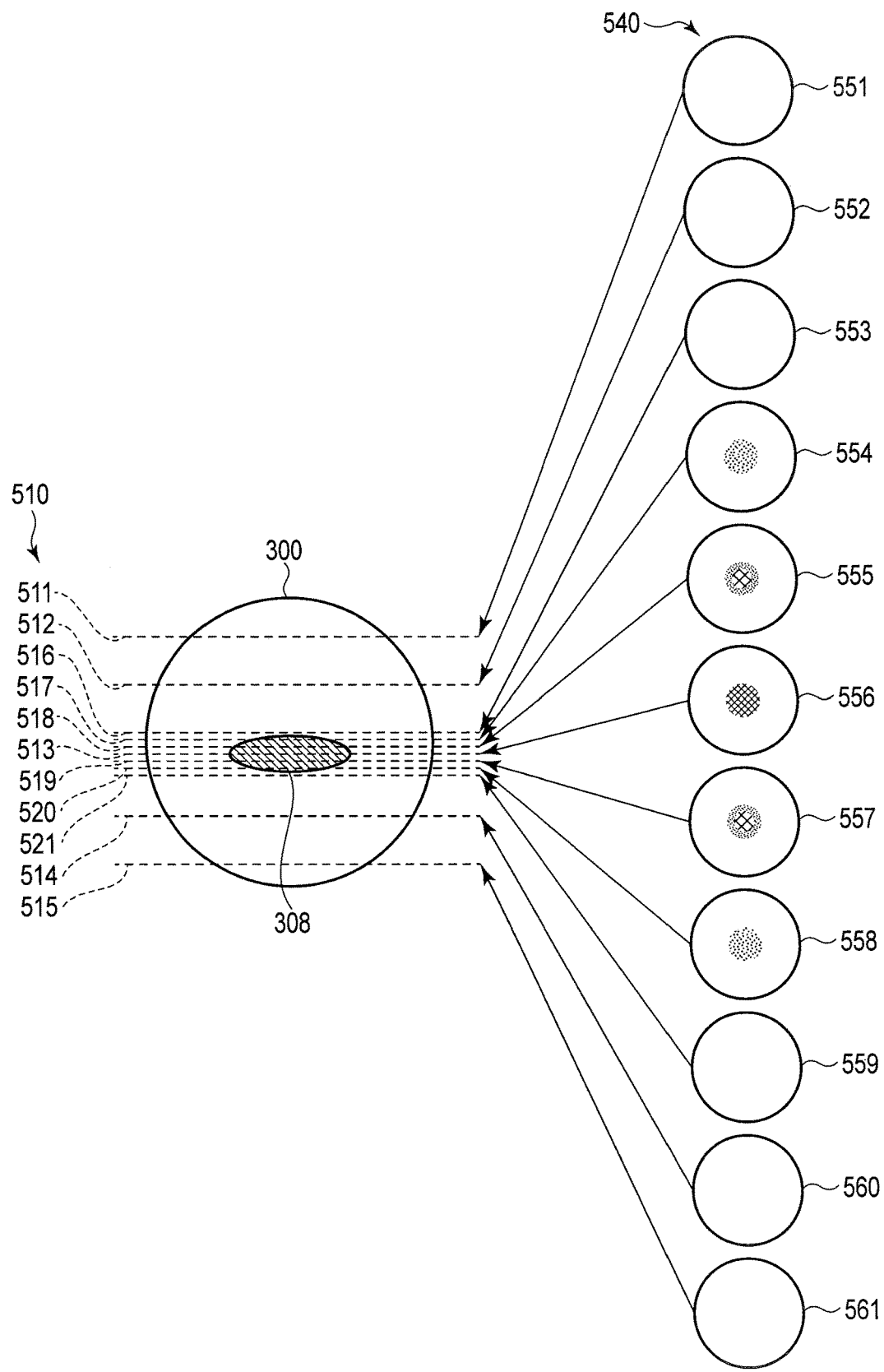
FIG. 20 is a schematic diagram for explaining how the interval between imaging planes is set according to the second embodiment.

The setting of imaging planes will be described with reference to FIGS. 19 and 20. In FIGS. 19 and 20, the left diagrams show the positional relationships between the imaging planes 510 of a three-dimensional sample 300. In the left diagrams in FIGS. 19 and 20, the horizontal broken lines indicate imaging planes 510. The diagrams show a state where the three-dimensional sample 300 contains a region of interest 308. In FIGS. 19 and 20, the right diagrams schematically illustrate two-dimensional images 540 obtained in the respective imaging planes 510.

FIG. 19 illustrates the case where the imaging plane 510 set in the initial image acquisition is arranged uniformly at the second intervals. To be more specific, in FIG. 19, a first imaging plane 511, a second imaging plane 512, a third imaging plane 513, a fourth imaging plane 514 and a fifth imaging plane 515 are set at equal focal intervals. Images obtained in the first imaging plane 511, second imaging plane 512, third imaging plane 513, fourth imaging plane 514 and fifth imaging plane 515 will be referred to as a first image 541, a second image 542, a third image 543, a fourth image 544 and a fifth image 545, respectively. Since the third imaging plane includes a region of interest 308, the third image 543 includes a bright region 549 in which the luminescence emission is imaged.

In the example shown in FIG. 19, the imaging condition determination unit 183 determines that the third image 543 includes the bright region 549 in the image luminescence analysis of step S601. In step S602, the imaging condition determination unit 183 determines that a region of interest is present in the neighborhood of the third imaging plane 513 of the imaging planes 510. In step S603, the imaging condition determination unit 183 sets a large number of imaging planes at short focal intervals in the neighborhood of the third imaging plane 513. FIG. 20 illustrates the imaging planes 510 set as above and two-dimensional images 540 obtained in those imaging planes 510.

In the example shown in FIG. 20, a sixth imaging plane 516, a seventh imaging plane 517, an eighth imaging plane 518, a ninth imaging plane 519, a tenth imaging plane 520 and an eleventh imaging plane 521 are set in the neighborhood of the third imaging plane 513, in addition to the first imaging plane 511, second imaging plane 512, third imaging plane 513, fourth imaging plane 514 and fifth imaging plane 515 described above. The focal interval between the adjacent ones of the sixth imaging plane 516, seventh imaging plane 517, eighth imaging plane 518, third imaging plane 513, ninth imaging plane 519, tenth imaging plane 520 and eleventh imaging plane 521 is the first interval, which is shorter than the second interval (e.g., the interval between the first imaging plane 511 and the second imaging plane 512) and which is less than the depth of focus.

As a result, a first image 551, a second image 552, a third image 553, a fourth image 554, a fifth image 555, a sixth image 556, a seventh image 557, an eighth image 558, a ninth image 559, a tenth image 560 and an eleventh image 561 are obtained in the first imaging plane 511, second imaging plane 512, sixth imaging plane 516, seventh imaging plane 517, eighth imaging plane 518, third imaging plane 513, ninth imaging plane 519, tenth imaging plane 520, eleventh imaging plane 521, fourth imaging plane 514 and fifth imaging plane 515, respectively. In this manner, detailed image data regarding the region of interest 308 can be obtained.

In the example shown in FIG. 20, the luminescence emitted from the region of interest 308 is not imaged in the third image 553 or the ninth image 559. In the subsequent imaging operation, therefore, image acquisition does not have to be performed with respect to the sixth imaging plane 516 and eleventh imaging plane 521 corresponding to the third image 553 and ninth image 559.

Turning back to FIG. 15, the image acquisition processing will be described again. After the imaging plane setting processing of step S502, the processing advances to step S503. In step S503, the controller 18 stands by and waits for the start of an imaging operation in consideration of the timings of the time-lapse imaging set in step S501.

Figure 21:
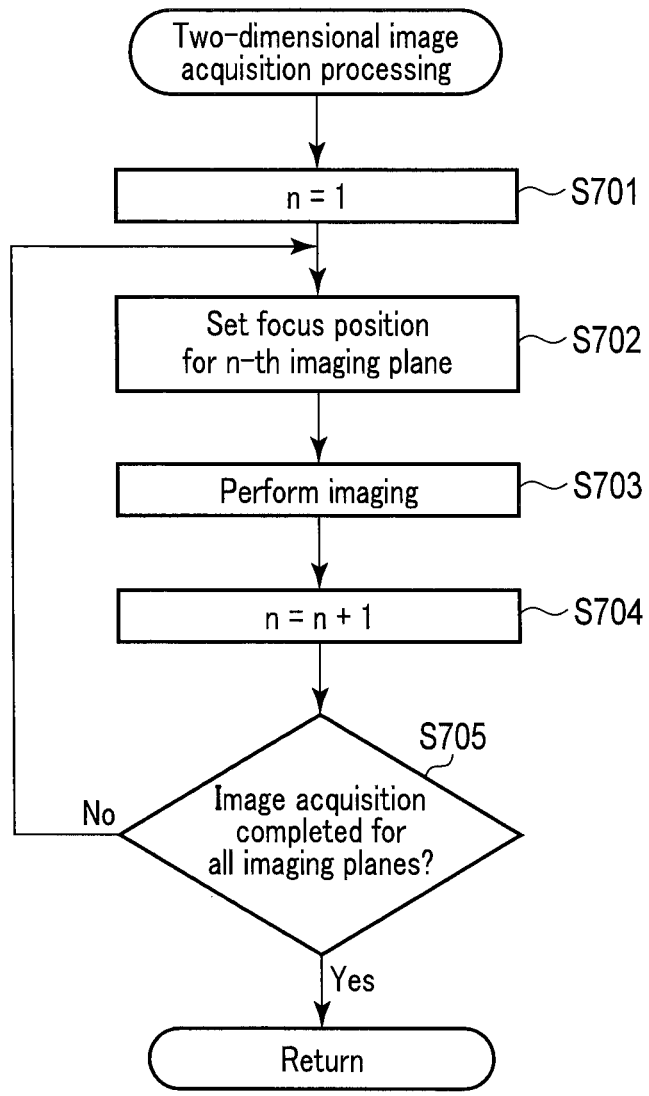
FIG. 21 is a flowchart illustrating an example of two-dimensional image acquisition processing according to the second embodiment.

In step S504, the imaging control unit 181 of the controller 18 performs two-dimensional image acquisition processing. In the two-dimensional image acquisition processing, a set of two-dimensional images are acquired in the imaging planes set in step S502, creating a two-dimensional image set. The two-dimensional image acquisition processing will be described with reference to the flowchart shown in FIG. 21.

In step S701, the imaging control unit 181 sets "1" as variable n.

In step S702, the imaging control unit 181 sets focus positions for the n-th imaging plane that is set in the imaging plane setting processing of step S502. To be more specific, the imaging control unit 181 controls the objective optical system drive unit 16 to adjust the position of the objective optical system 14, for example the position of the objective lens 142, so that images can be acquired in the n-th imaging plane.

In step S703, the imaging control unit 181 causes the imaging unit to perform imaging operations, thereby acquiring two-dimensional images.

In step S704, the imaging control unit 181 sets "n+1" as variable n.

In step S705, the imaging control unit 181 determines whether image acquisition is completed for all imaging planes that are set in the imaging plane setting processing of step S502. If the image acquisition is not completed, the processing returns to step S702. That is, the imaging plane is changed, and a two-dimensional image is acquired in the new imaging plane. If the image acquisition is completed, the two-dimensional image acquisition processing is ended, and the processing returns to the image acquisition processing described with reference to FIG. 15.

In step S505, the image synthesis unit 182 of the controller 18 generates a three-dimensional image based on the two-dimensional images acquired in the two-dimensional image acquisition processing of step S504.

In step S506, the controller 18 determines whether or not the next image acquisition of the time-lapse imaging is required based on the initial settings determined in step S501. If the next image acquisition is required, the processing returns to step S502. At the timing for the next image acquisition of the time-lapse imaging, two-dimensional images are acquired in a newly set imaging plane, and a three-dimensional image is acquired based on the two-dimensional images. If it is determined in step S506 that the next image acquisition is not required, the image acquisition processing is brought to an end.

As described above, two-dimensional images of regions of interest in which luminescence is detected are acquired as first two-dimensional images, and two-dimensional images of the other regions are acquired as second two-dimensional images. The interval between a first two-dimensional image and a two-dimensional image adjacent to that first two-dimensional image is set as a first interval, and the interval between a second two-dimensional image and a second two-dimensional image adjacent to that second two-dimensional image is set as a second interval. The first interval is shorter than the second interval. In particular, the first interval is equal to or less than the depth of focus of the objective optical system 14.

In the present embodiment, the number of two-dimensional images to be acquired changes in accordance with the luminescent state of the three-dimensional sample. Therefore, the time required for the acquisition of the determined number of two-dimensional images changes when the time-lapse imaging is being performed. Therefore, the time required for acquiring a set of two-dimensional images may be longer than the time between the start of the acquisition of the set of two dimensional-images and the start of the acquisition of the next set of two-dimensional images. Therefore, when the focal interval between imaging planes is set at the first interval, which is less than the depth of focus of the objective optical system 14, the time between the start of the acquisition of a set of two-dimensional images and the start of the acquisition of the next set of two-dimensional images should be preferably longer than the time required for acquiring the set of two-dimensional images.

In the present embodiment, where no luminescence is detected, namely where there is no noteworthy phenomenon inside the three-dimensional sample 300, the focal interval between imaging planes is set at the second interval, which is more than the depth of focus of the objective optical system 14, and a small number of two-dimensional images are used for reconstructing one three-dimensional image. As a result, the data size is decreased.

Where luminescence is detected, namely where there is a noteworthy phenomenon inside the three-dimensional sample 300, the focal interval between imaging planes is set at the first interval, which is equal to or less than the depth of focus of the objective optical system 14, and a highly-precise three-dimensional image is obtained. With respect to a region where no luminescence is detected, namely a region where there is no noteworthy phenomenon inside the three-dimensional sample 300, the focal interval between imaging planes is set at the second interval, which is more than the depth of focus of the objective optical system 14, and a small number of two-dimensional images are used for reconstructing one three-dimensional image. As a result, the data size is decreased.

As described above, both the reduction of data size and the necessary and sufficient high-resolution data are compatible. As a result, the three-dimensional sample can be analyzed in a short time and with high accuracy.

Since unnecessary data is decreased and only necessary data is acquired, the time for data acquisition and the time for subsequent data analysis can be shortened. Where the medicinal effect and toxicity of a new drug are evaluated using embryoid bodies or spheroids derived from stem cells, and where the differentiation process in which embryoid bodies derived from stem cells differentiate into various cells is evaluated and monitored, data acquisition and data analysis can be performed smoothly, and quick evaluation is thus enabled. In particular, where the change of a region of interest (ROI) designated in a given imaging plane is larger than a predetermined threshold, or where the change of the luminescence intensity for the entire imaging plane is larger than a predetermined threshold, the focal interval between the imaging planes can be shortened, and the information on gene expression can be selectively increased.

First Modification of Second Embodiment

Figure 22:
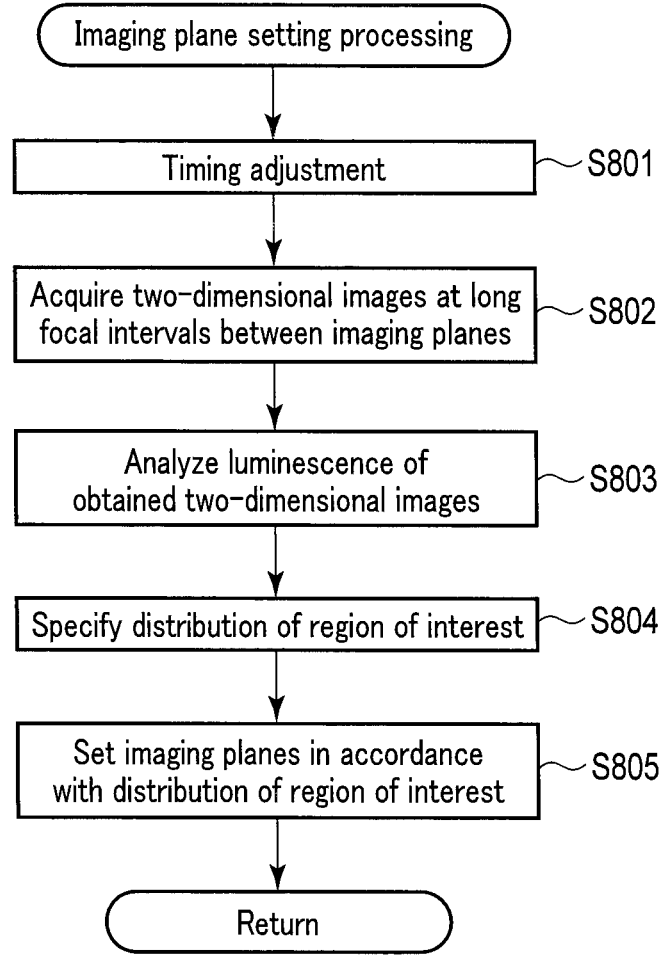
FIG. 22 is a flowchart illustrating an example of imaging plane setting processing according to the first modification of the second embodiment.

The first modification of the second embodiment will be described. In the description below, reference will be made to how the modification differs from the second embodiment. Therefore, the same symbols will be used to denote structural elements similar or corresponding to those of the second embodiment, and a description of such structural elements will be omitted. In connection with the above embodiment, reference was made to the case where a region of interest is specified based on two-dimensional images of the preceding image acquisition. However, this is not restrictive. For example, as described in the flowchart shown in FIG. 22, two-dimensional images may be acquired at focal intervals which are longer than the imaging-plane focal intervals applied to the regions other than a region of interest, and the distribution of the region of interest may be specified based on the two-dimensional images.

In step S801, the imaging condition determination unit 183 is made to stand by and adjusts the timing to start the next processing, such that the setting of imaging planes ends before the start of the next acquisition of two-dimensional images. In step S802, the imaging condition determination unit 183 acquires two-dimensional images at long focal intervals between imaging planes in cooperation of the imaging control unit 181. The focal intervals may be third intervals which are longer than the second intervals. A set of two-dimensional images thus obtained will be referred to as an evaluation image group. The imaging condition determination unit 183 analyzes the luminescence of the two-dimensional images of the evaluation image group obtained in step S803, and specifies the distribution of a region of interest in step S804. In step S805, the imaging condition determination unit 183 sets imaging planes in accordance with the distribution of the region of interest.

This modification is advantageous in that imaging planes can be set in accordance with the current state of the three-dimensional sample 300 even if the time intervals at which the time-lapse imaging is performed is long.

Second Modification of Second Embodiment

The second modification of the second embodiment will be described. In the description below, reference will be made to how the modification differs from the second embodiment. Therefore, a description of structural elements similar or corresponding to those of the second embodiment will be omitted. In the above embodiment, the number of imaging planes which are set changes in accordance with how a region of interest changes. However, when the number of imaging planes changes, the number of two-dimensional images included in one set of two-dimensional images also changes, accordingly. In the present modification, the number of imaging planes is predetermined. To be more specific, in the imaging plane setting processing, imaging planes are set such that the total number of imaging planes is predetermined in accordance with a region of interest.

According to the present modification, the total of exposure times required for acquiring a set of two-dimensional images is constant. As a result, the time-lapse imaging time interval is prevented from becoming shorter than the time interval at which a set of two-dimensional images are acquired.

Third Modification of Second Embodiment

The third modification of the second embodiment will be described. In the description below, reference will be made to how the modification differs from the second embodiment. Therefore, the same symbols will be used to denote structural elements similar or corresponding to those of the second embodiment, and a description of such structural elements will be omitted. In the embodiment described above, the focal interval between imaging planes is set such that it is the first interval (which is equal to or less than the depth of focus of the objective optical system 14) in regions of interest and is the second interval (which is more than the depth of focus) in the other regions. However, this is not restrictive. A plurality of other focal intervals between imaging planes may be used, and a combination of these can be properly used. Needless to say, the focal interval between imaging planes should be short in regions where the degree of attention is high, as in a region where the luminescence to be observed is high or in a region where the luminescence intensity changes greatly, and should be long in regions where the degree of attention is low. In either case, the focal intervals between imaging planes may be less than the depth of focus of the objective optical system 14. In this modification as well, three-dimensional images acquired have a necessary resolution and yet have a decreased data size.

The adjustment of the imaging pitch described in connection with the first embodiment and the adjustment of the imaging time interval described in connection with the second embodiment may be combined. The present invention is applicable not only to samples for regenerative medicine but also to various samples for which the gene expression in each cell requires time-lapse observation. For example, the present invention may be applicable to an in vivo sample. The imaging pitch adjustment and/or the imaging time interval adjustment, which were described as being made by the imaging system, may be made by the user. That is, the user manually changes the imaging conditions while looking at what is displayed on the display of the imaging system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for generating a three-dimensional luminescence image, the method comprising:
    setting a focal interval between two-dimensional images in accordance with localization of luminescence in the three-dimensional sample, the three-dimensional sample containing a plurality of cells prepared to be luminescent and having a three-dimensional shape, the two-dimensional images having mutually different focal planes;
    acquiring a two-dimensional image set including the two-dimensional images at the set focal interval by imaging the three-dimensional sample under an unirradiated condition; and
    generating a three-dimensional luminescence image by combining the two-dimensional images included in the two-dimensional image set together;
    wherein where the two-dimensional images of the two-dimensional image set are assumed to include a first two-dimensional image in which luminescence satisfying a predetermined condition is detected and a second two-dimensional image other than the first two-dimensional image, the focal interval between the two-dimensional images is set such that a first interval between the first two-dimensional image and a two-dimensional image adjacent to that first two-dimensional image is shorter than a second interval between the second two-dimensional image and a second two-dimensional image adjacent to that second two-dimensional image.

2. The method according to claim 1, wherein the predetermined condition is that a luminescence intensity of the luminescence of the two-dimensional image is not less than a predetermined value.

3. The method according to claim 1, wherein the predetermined condition is that an area value of a region in which the luminescence of the two-dimensional image is shown is not less than a predetermined value.

4. The method according to claim 1, wherein the predetermined condition is that a change of a luminescence intensity of the luminescence is not less than a predetermined value in a predetermined region of the two-dimensional image.

5. The method according to claim 1, further comprising: acquiring an evaluation image group including the two-dimensional images at a focal interval longer than the first interval; and determining whether or not the predetermined condition is satisfied, based on the evaluation image group.

6. The method according to claim 1, wherein the first interval is not more than a depth of focus of an objective optical system used for acquiring the two-dimensional images.

7. A method for generating a three-dimensional luminescence image, the method comprising:

setting a focal interval between two-dimensional images in accordance with localization of luminescence in the three-dimensional sample, the three-dimensional sample containing a plurality of cells prepared to be luminescent and having a three-dimensional shape, the two-dimensional images having mutually different focal planes;

acquiring a two-dimensional image set including the two-dimensional images at the set focal interval by imaging the three-dimensional sample under an unirradiated condition; and generating a three-dimensional luminescence image by combining the two-dimensional images included in the two-dimensional image set together;

wherein the two-dimensional image set is repeatedly acquired a number of times, and the focal interval is set each time the two-dimensional image set is acquired; and even where the focal interval between the two-dimensional images changes, a total of exposure times for which the two-dimensional images of the two-dimensional image set are acquired is unchanged.

8. The method according to claim 7, wherein the focal interval is set based on the two-dimensional image set that is acquired last.

9. The method according to claim 7, wherein the two-dimensional image set is acquired by repeating identical processing at constant time intervals.

* * * * *

UNITED STATES PATENT AND TRADEMARK OFFICE
CERTIFICATE OF CORRECTION

PATENT NO.        : 10,401,276 B2
APPLICATION NO.   : 15/647486
DATED             : September 3, 2019
INVENTOR(S)       : Taro Hayashi and Yoko Ohashi Page 1 of 1

It is certified that error appears in the above-identified patent and that said Letters Patent is hereby corrected as shown below:

On the Title Page

Item (63) should read:
Related U.S. Application Data
(63) Continuation of Application No. PCT/JP2016/051679, filed on January 21, 2016

Signed and Sealed this
Thirty-first Day of December, 2019

Andrei Iancu
*Director of the United States Patent and Trademark Office*